(12) United States Patent
Ikehashi et al.

(10) Patent No.: US 10,794,886 B2
(45) Date of Patent: Oct. 6, 2020

(54) GAS DETECTION DEVICE

(71) Applicant: KABUSHIKI KAISHA TOSHIBA, Tokyo (JP)

(72) Inventors: Tamio Ikehashi, Yokohama Kanagawa (JP); Hiroaki Yamazaki, Yokohama Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 16/366,162

(22) Filed: Mar. 27, 2019

(65) Prior Publication Data
US 2019/0219552 A1 Jul. 18, 2019

Related U.S. Application Data

(62) Division of application No. 15/243,611, filed on Aug. 22, 2016, now Pat. No. 10,281,444.

(30) Foreign Application Priority Data

May 30, 2016 (JP) .................................. 2016-107802

(51) Int. Cl.
*G01N 33/00* (2006.01)
*G01B 7/16* (2006.01)

(52) U.S. Cl.
CPC .......... *G01N 33/0036* (2013.01); *G01B 7/22* (2013.01); *G01N 33/005* (2013.01); *G01N 33/0047* (2013.01)

(58) Field of Classification Search
CPC .......... G01N 33/0036; G01N 33/0047; G01N 33/005; G01B 7/22
See application file for complete search history.

(56) References Cited

U.S. PATENT DOCUMENTS 7,258,020 B2 8/2007 Silverbrook et al.
7,340,941 B1 3/2008 Fruhberger et al.
(Continued)

FOREIGN PATENT DOCUMENTS

CN 101492149 A * 7/2009
EP 2169400 A1 3/2010
(Continued)

OTHER PUBLICATIONS

Japanese Office Action dated Jul. 16, 2019, mailed in counterpart Japanese Application No. 2016-107802, 8 pages (with translation).

*Primary Examiner* — John Fitzgerald
(74) *Attorney, Agent, or Firm* — Kim & Stewart LLP

(57) ABSTRACT

A gas detection device includes a substrate having a main surface and a movable film structure located on, and including a portion thereof spaced from, the main surface of the substrate. The portion of the movable film structure located over and spaced from the substrate includes a first film formed of an insulating material, a patterned second film which deforms as a result of absorbing or adsorbing a predetermined gas, and a patterned third film comprising a resistive heater, at least a portion of the movable film structure spaced from the substrate being movable with respect to the substrate. From the perspective of a direction perpendicular to the main surface of the substrate, at least a portion of a pattern of the second film overlaps at least a portion of a pattern of the third film.

20 Claims, 31 Drawing Sheets

(56) References Cited

U.S. PATENT DOCUMENTS

| | | |
|---|---|---|
| 7,430,897 B2 | 10/2008 | Hu et al. |
| 8,921,958 B2 | 12/2014 | Ikehashi |
| 9,823,211 B1 | 11/2017 | Allen |
| 2004/0169243 A1 | 9/2004 | Tao et al. |
| 2006/0055392 A1 | 3/2006 | Passmore et al. |
| 2006/0248950 A1 | 11/2006 | Silverbrook et al. |
| 2006/0267109 A1 | 11/2006 | Ohguro |
| 2007/0024410 A1 | 2/2007 | Yazdi |
| 2007/0039392 A1 | 2/2007 | Silverbrook et al. |
| 2007/0062295 A1 | 3/2007 | Silverbrook et al. |
| 2008/0173095 A1 | 7/2008 | Silverbrook et al. |
| 2008/0178666 A1 | 7/2008 | Silverbrook et al. |
| 2009/0158854 A1 | 6/2009 | Silverbrook et al. |
| 2011/0261359 A1 | 10/2011 | Inada et al. |
| 2013/0311108 A1 | 11/2013 | Stetter et al. |
| 2015/0040674 A1 | 2/2015 | Ishihara et al. |
| 2016/0363553 A1 | 12/2016 | Alexeenko et al. |
| 2016/0377569 A1 | 12/2016 | Rajaraman et al. |

FOREIGN PATENT DOCUMENTS

| | | | |
|---|---|---|---|
| JP | S6235253 A | | 2/1987 |
| JP | H02259458 A | | 10/1990 |
| JP | H03272444 A | | 12/1991 |
| JP | 2007045756 A | | 2/2007 |
| JP | 2007132762 A | | 5/2007 |
| JP | 2012119821 A | * | 6/2012 |
| JP | 2014132232 A | | 7/2014 |
| JP | 5813471 B2 | | 11/2015 |

\* cited by examiner

GAS DETECTION DEVICE

CROSS-REFERENCE TO RELATED APPLICATION

This application is a division of U.S. patent application Ser. No. 15/243,611, filed on Aug. 22, 2016, now U.S. Pat. No. 10,281,444, granted on May 7, 2019, which is based upon and claims the benefit of priority from Japanese Patent Application No. 2016-107802, filed May 30, 2016, the entire contents of each of which are incorporated herein by reference.

FIELD

Exemplary embodiments described herein relate generally to a gas detection device.

BACKGROUND

Generally, gas detection devices, which are formed using microelectro-mechanical systems (MEMS) technology and detect gases such as a hydrogen gas, are proposed. It cannot necessarily be said that the gas detection devices in the related art have satisfactory performance.

DETAILED DESCRIPTION

A gas detection device having satisfactory performance is provided.

According to one embodiment, there is provided a gas detection device including a substrate having a main surface, and a movable film structure located on, and including a portion thereof spaced from, the main surface of the substrate. The portion of the movable film structure located over and spaced from the substrate includes a first film formed of an insulating material, a patterned second film which deforms as a result of absorbing or adsorbing a predetermined gas, and a patterned third film comprising a resistive heater, at least a portion of the movable film structure spaced from the substrate being movable with respect to the substrate. From the perspective of a direction perpendicular to the main surface of the substrate, at least a portion of a pattern of the second film overlaps at least a portion of a pattern of the third film.

Hereinafter, embodiments will be described with reference to the accompanying drawings.

Embodiment 1

First, a gas detection device of a first embodiment will be described. The gas detection device of the embodiment is used as a hydrogen gas detection device, and is manufactured using microelectro-mechanical systems (MEMS) technology.

Figure 1A:
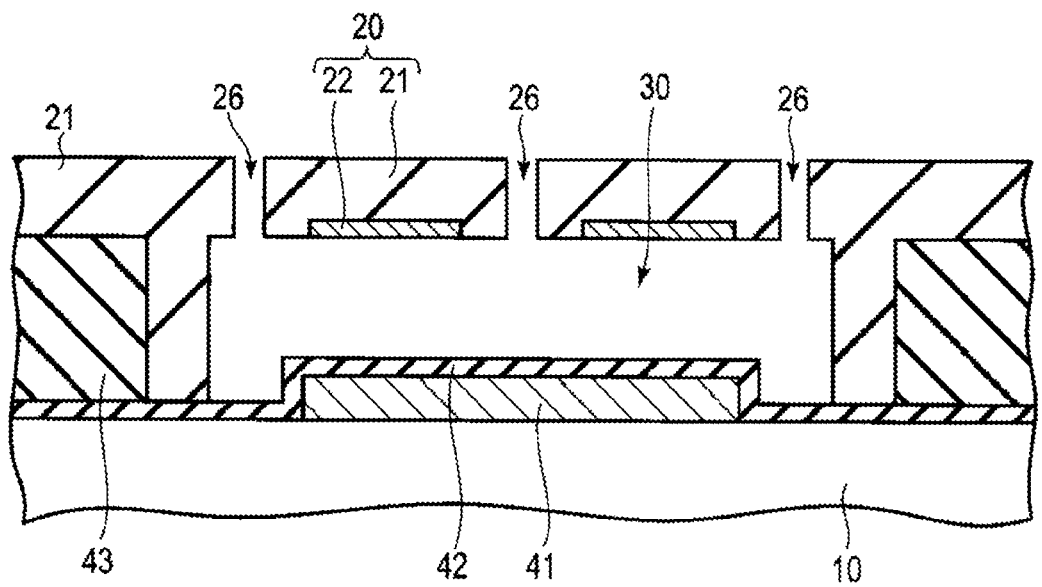
FIG. 1A is a schematic sectional view illustrating a configuration of a gas detection device of a first embodiment.
Figure 2:
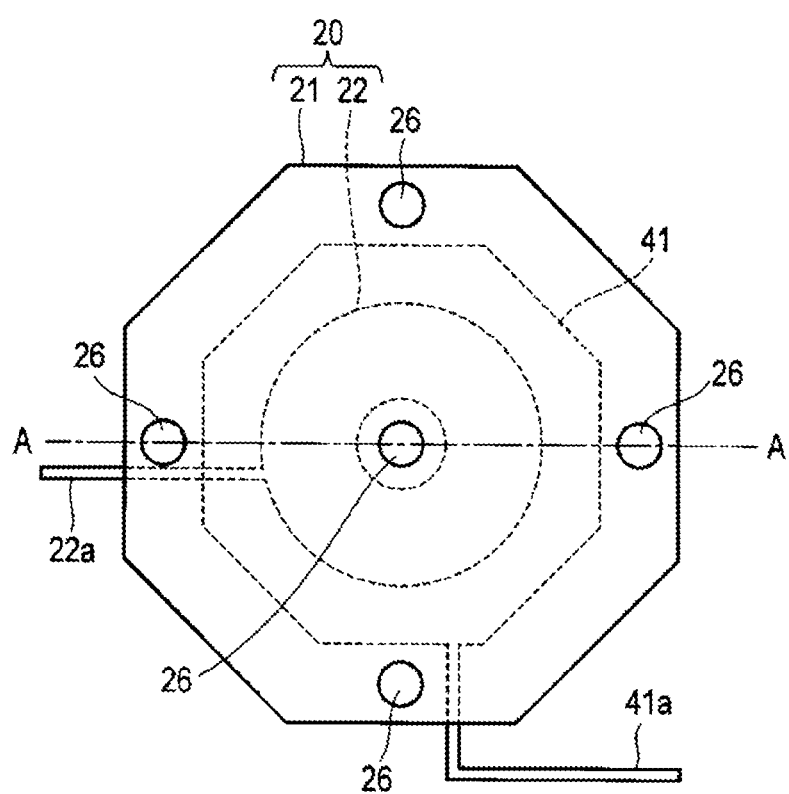
FIG. 2 is a schematic top view illustrating the configuration of the gas detection device of the first embodiment.

FIG. 1A is a schematic sectional view illustrating a configuration of the gas detection device (hydrogen gas detection device) of the embodiment. FIG. 2 is a schematic top view illustrating the configuration of the gas detection device (hydrogen gas detection device) of the embodiment. A section taken along line A-A in FIG. 2 substantially corresponds to FIG. 1A.

The gas detection device illustrated in FIGS. 1A and 2 includes a substrate 10; a movable film structure 20 provided above the substrate 10; and a first conductive portion 41 provided on the substrate 10, and which acts as a first electrode (lower electrode or fixed electrode) of a variable capacitor. A cavity 30 is formed inside the movable film structure 20 between a portion of the substrate 10 and a portion of the movable film structure 20.

The substrate 10 contains a circuit area containing a semiconductor substrate (for example, silicon substrate), a MOS transistor, wirings, and the like.

The movable film structure 20 includes a brittle material film (first film) 21 formed of a brittle material, and a hydrogen absorption material film (second film) 22 formed of a hydrogen absorbing material (hydrogen storage material). In the embodiment, the hydrogen absorption material film 22 is provided on a lower surface of the brittle material film 21. The hydrogen absorption material film 22 acts as a second electrode (upper electrode or movable electrode) of the variable capacitor, and is electrically connected to an external circuit via a lead wiring 22a. The movable film structure 20 includes multiple through holes (vent holes) 26 which lead to the cavity 30. Specifically, multiple through holes 26 are formed in the brittle material film 21. The inner pressure and the outer pressure of the movable film structure 20 are kept the same by the through holes 26.

The brittle material film (first film) 21 acts as a base film of the movable film structure 20. The brittle material film 21 is preferably formed of a material containing silicon (Si). The material of the brittle material film 21 may be an insulating material or a conductive material. Specifically, the following material is preferably used as the material of the brittle material film 21: silicon (Si); silicon nitride (typically, a material containing silicon (Si) and nitrogen (N)); silicon oxide (typically, a material containing silicon (Si) and oxygen (O)); or silicon carbide (typically, a material containing silicon (Si) and carbon (C)). AlTi (typically, a material containing aluminum (Al) and titanium (Ti)) or the like may also be used as the material of the brittle material film 21. In the embodiment, a silicon nitride film (SiN film) is used as the brittle material film 21.

The hydrogen absorption material film (hydrogen storage material film or second film) 22 acts as a hydrogen detection film of the movable film structure 20. The material of the hydrogen absorption material film 22 is preferably selected from palladium (Pd), an alloy containing palladium (Pd), an alloy containing titanium (Ti), and an alloy containing lanthanum (La). In the embodiment, a palladium film (Pd film) or a palladium alloy film (Pd alloy film) is used as the hydrogen absorption material film 22. A palladium-nickel alloy film (Pd—Ni alloy film) or a palladium-silver alloy film (Pd—Ag alloy film) is used as a palladium alloy film.

The first conductive portion 41 acts as the first electrode (lower electrode or fixed electrode) of the variable capacitor, and is electrically connected to the external circuit via a lead wiring 41a. The first conductive portion 41 faces the hydrogen absorption material film 22 acting as the second electrode (upper electrode or movable electrode) of the movable capacitor. The first conductive portion 41 and the substrate 10 are covered with an insulating film 42. An interlayer insulating film 43 is provided on the insulating film 42.

As described above, the movable film structure 20 includes the brittle material film 21 acting as a base film, and the hydrogen absorption material film 22 acting as a hydrogen detection film. It is possible to obtain a gas detection device having good characteristics by adopting the movable film structure 20 including the brittle material film 21 and the hydrogen absorption material film 22. Hereinafter, additional description will be given.

If the hydrogen absorption material film 22 absorbs (stores) hydrogen, the hydrogen absorption material film 22 expands (the volume increases). For this reason, if the hydrogen absorption material film 22 absorbs hydrogen, the movable film structure 20 is deformed, and a distance between the first conductive portion (lower electrode of the variable capacitor) 41 and the hydrogen absorption material film (upper electrode of the variable capacitor) 22 changes. Since the amount of expansion of the hydrogen absorption material film 22 changes according to the amount of absorbed hydrogen, the distance between the first conductive portion (lower electrode) 41 and the hydrogen absorption material film (upper electrode) 22 changes according to the amount of absorbed hydrogen. Therefore, the capacitance of the variable capacitor changes according to the amount of hydrogen absorbed by the hydrogen absorption material film 22. As a result, it is possible to calculate the amount of absorbed hydrogen by obtaining the capacitance or change in capacitance of the variable capacitor. That is, it is possible to calculate the concentration of hydrogen in the vicinity of the hydrogen absorption material film 22 by obtaining the capacitance or change in capacitance of the variable capacitor.

If the base film of the movable film structure 20 is deformed due to creep fatigue or the like, it is difficult to detect the concentration of hydrogen based on the deformation of the hydrogen absorption material film 22. In the embodiment, because a brittle material film 21 is used as the base film of the movable film structure 20, there is almost no deformation of the base film as a result of creep fatigue or the like, but the brittle material can sufficiently deform without breaking or cracking to allow a change in the relative position of the electrodes of the variable capacitor. For this reason, in the embodiment, it is possible to detect the concentration of hydrogen with high accuracy, based on deformation of the hydrogen absorption material film 22. As a result, in the embodiment, it is possible to obtain a high-performance gas detection device (hydrogen gas detection device) having good detection accuracy and good reliability.

In the embodiment, since the movable film structure 20 is provided with the multiple through holes 26 which lead to the cavity 30, the inner pressure and the outer pressure of the movable film structure 20 are kept the same. If the through holes 26 are not provided, the movable film structure 20 may be deformed due to a pressure difference between the inside and the outside of the movable film structure 20, and it may not be possible to accurately detect the concentration of hydrogen, which is a problem. In the embodiment, since the through holes 26 are provided in the movable film structure 20, it is possible to accurately detect the concentration of hydrogen.

Figure 1B:
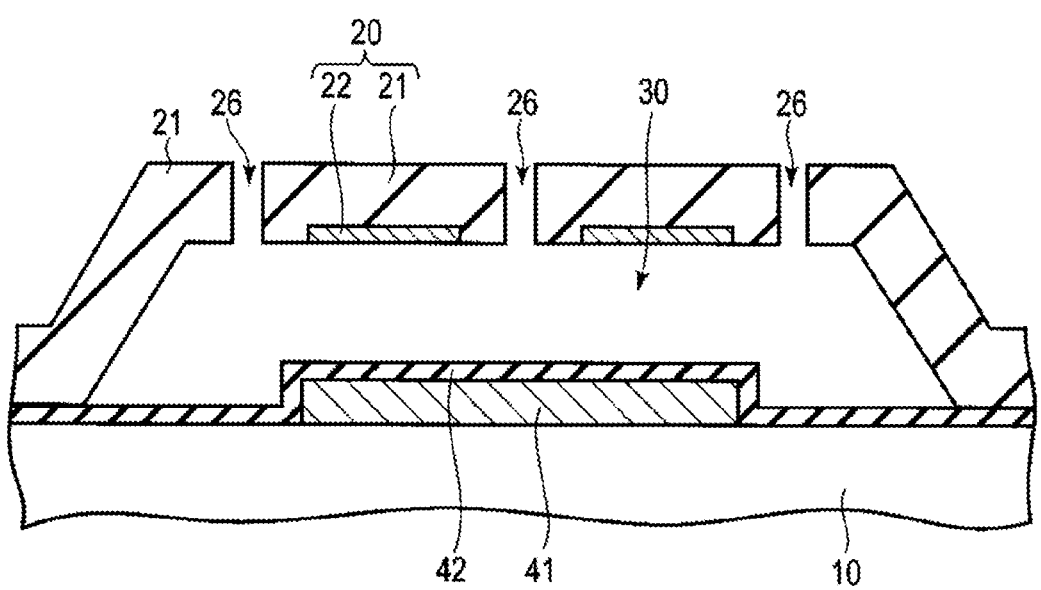
FIG. 1B is a schematic sectional view illustrating another configuration of the gas detection device of the first embodiment.

FIG. 1B is a schematic sectional view illustrating another configuration of the gas detection device of the embodiment. In the configuration illustrated in FIG. 1A, the interlayer insulating film 43 is provided, and thus, it is possible to obtain the movable film structure 20 having high strength. In the configuration illustrated in FIG. 1B, the interlayer insulating film 43 is not provided, planarization is not required, and it is possible to simplify manufacturing.

Figure 3:
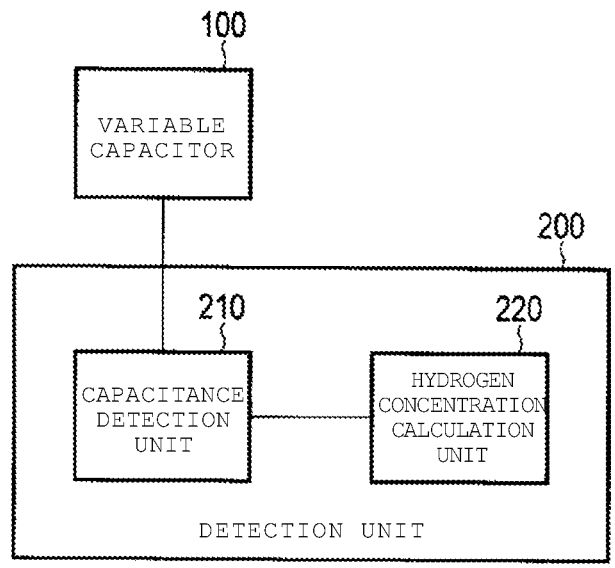
FIG. 3 is a block diagram illustrating the entire configuration of the gas detection device of the first embodiment.

FIG. 3 is a block diagram illustrating the entire configuration of the gas detection device (hydrogen gas detection device) of the embodiment. As illustrated in FIG. 3, a detection unit 200 is connected to a variable capacitor 100 having the aforementioned structure. The detection unit 200 may be provided in the substrate 10 illustrated in FIG. 1A, or may be provided separate from the substrate 10. The detection unit 200 includes a capacitance detection unit 210 that detects the capacitance of the variable capacitor 100, and a hydrogen concentration calculation unit 220 that calculates the concentration of hydrogen based on the capacitance detected by the capacitance detection unit 210. It is possible to calculate the concentration of hydrogen with high accuracy using the hydrogen concentration calculation unit 220 by obtaining a relationship between the capacitance of the variable capacitor and the concentration of hydrogen in advance.

Hereinafter, various modification examples of the gas detection device (hydrogen gas detection device) of the embodiment will be described. Each of the following modification examples has the same basic configuration as the configuration of the embodiment. Therefore, description of matters which have already been described in the embodiment will be omitted.

Figure 4:
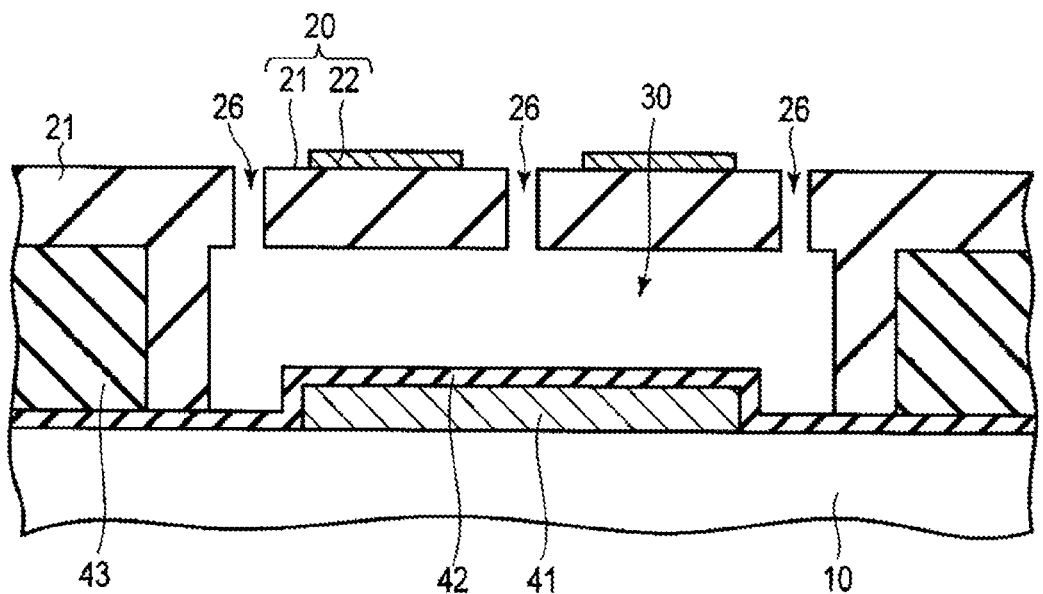
FIG. 4 is a schematic sectional view illustrating a configuration of a gas detection device in a first modification example of the first embodiment.
Figure 5:
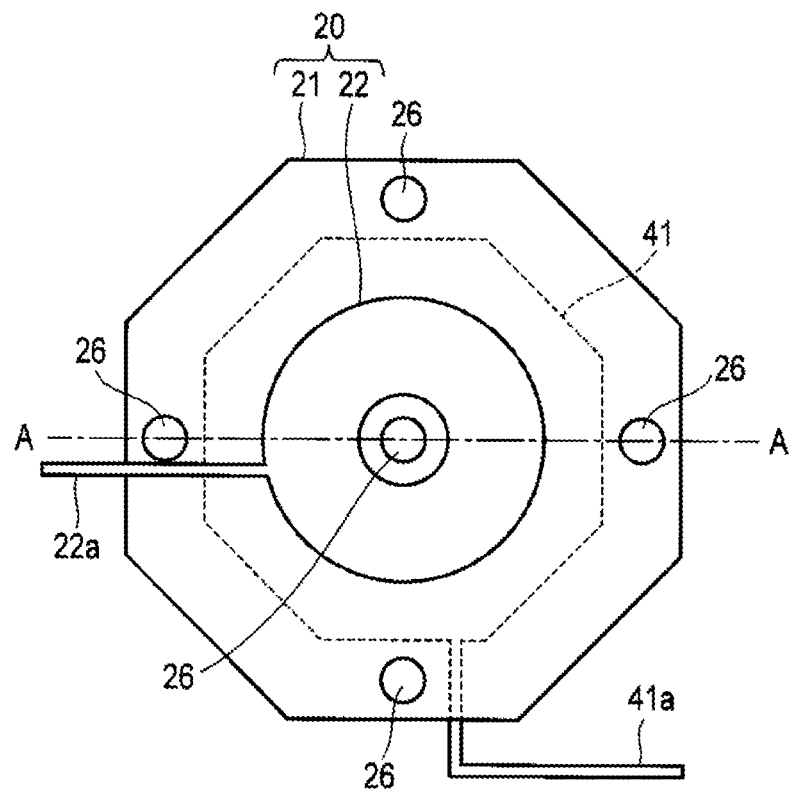
FIG. 5 is a schematic top view illustrating the configuration of the gas detection device in the first modification example of the first embodiment.

FIG. 4 is a schematic sectional view illustrating a configuration of a gas detection device in a first modification example of the embodiment. FIG. 5 is a schematic top view illustrating the configuration of the gas detection device in the first modification example of the embodiment.

In the embodiment, the hydrogen absorption material film 22 is provided on the lower surface of the brittle material film 21. In contrast, in the modification example, the hydrogen absorption material film 22 is provided on an upper surface of the brittle material film 21. The rest of the configuration is the same as that of the embodiment.

Figure 6:
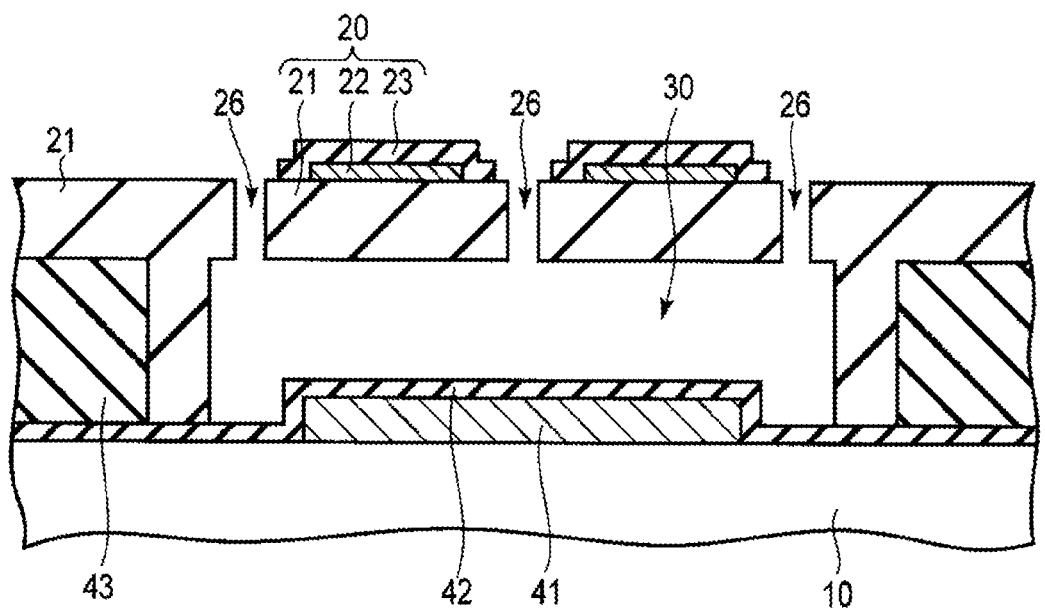
FIG. 6 is a schematic sectional view illustrating a configuration of a gas detection device in a second modification example of the first embodiment.
Figure 7:
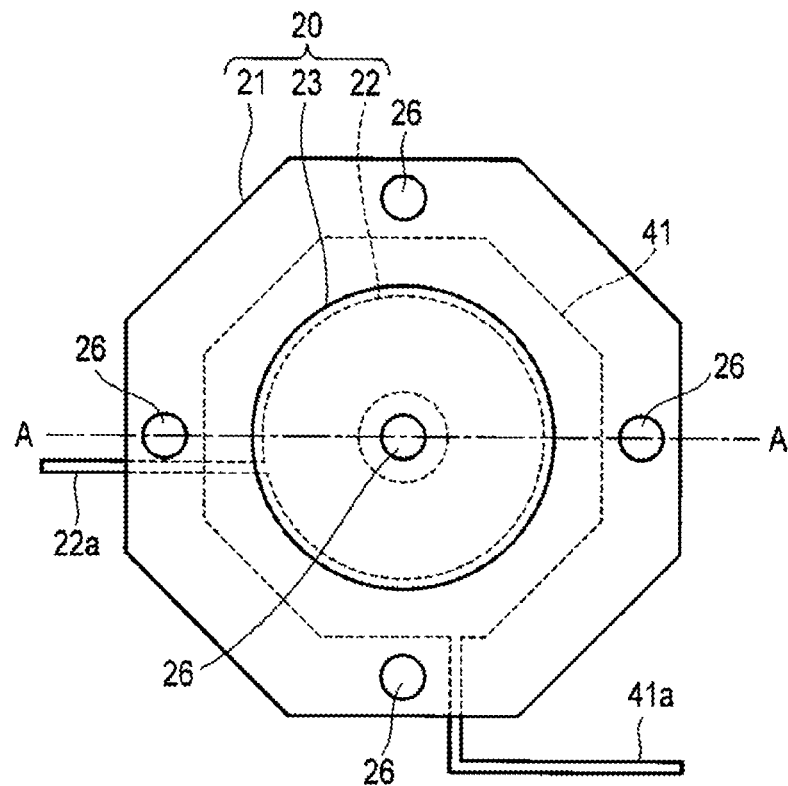
FIG. 7 is a schematic top view illustrating the configuration of the gas detection device in the second modification example of the first embodiment.

FIG. 6 is a schematic sectional view illustrating a configuration of a gas detection device in a second modification example of the embodiment. FIG. 7 is a schematic top view illustrating the configuration of the gas detection device in the second modification example of the embodiment.

In the modification example, the movable film structure 20 further includes a moisture infiltration preventive film 23 that covers the hydrogen absorption material film 22 and prevents the infiltration of moisture into the hydrogen absorption material film 22. Specifically, a moisture-proof film or a hydrophobic film may be used as the moisture infiltration preventive film 23. A silicon nitride film (SiN film), a gold film (Au film), a platinum film (Pt film), or the like may be used as the moisture infiltration preventive film 23. It is possible to prevent the infiltration of moisture from causing deterioration of characteristics of the hydrogen absorption material film 22 by providing the moisture infiltration preventive film 23. The moisture infiltration preventive film 23 prevents the infiltration of moisture into the hydrogen absorption material film 22, but allows the penetration of hydrogen. As a result, similar to the embodiment, it is possible to detect the concentration of hydrogen in an adjacent ambient environment.

Figure 8A:
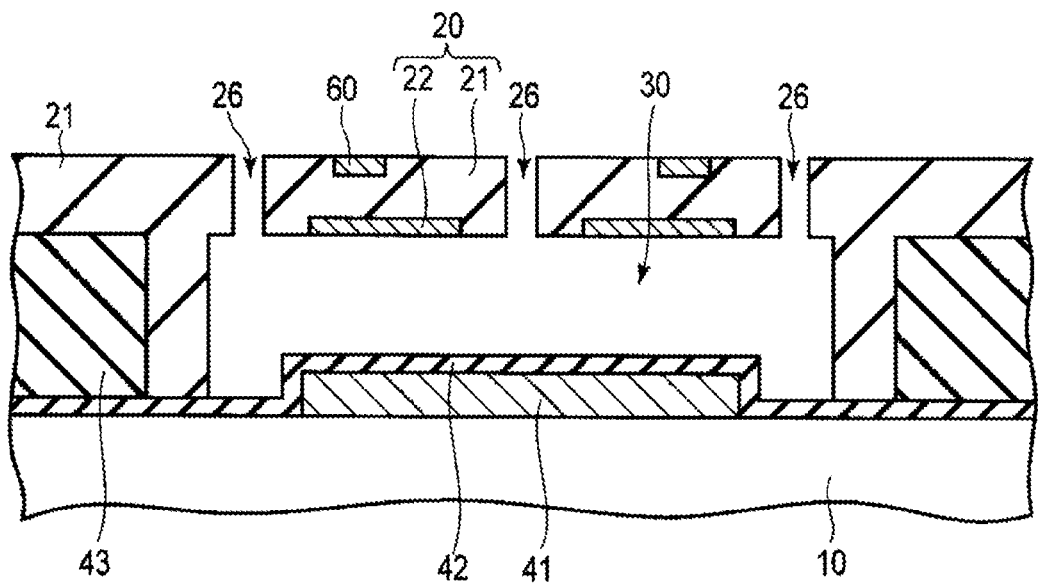
FIG. 8A is a schematic sectional view illustrating a configuration of a gas detection device in a third modification example of the first embodiment.
Figure 8B:
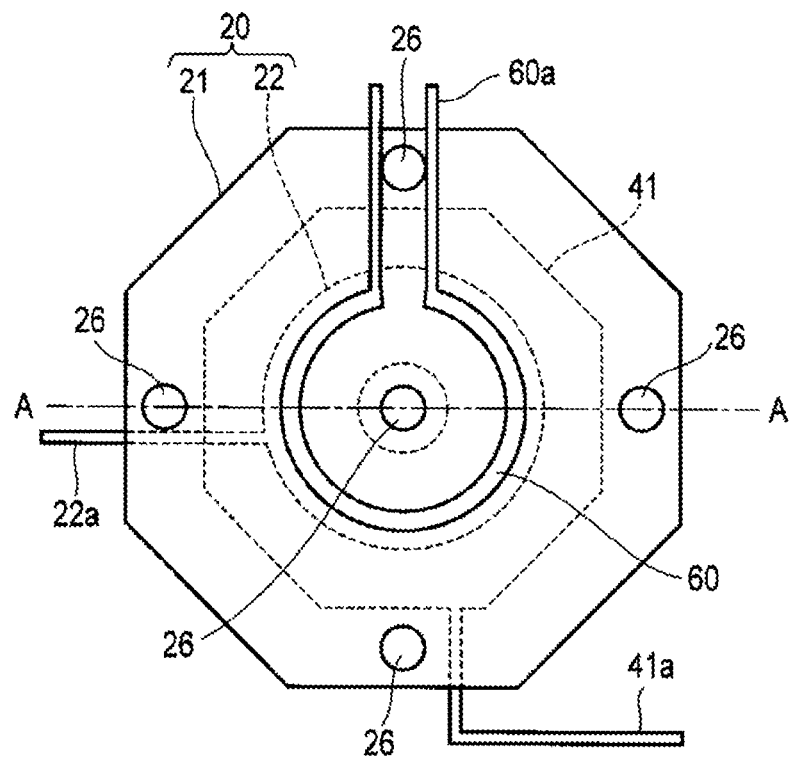
FIG. 8B is a schematic top view illustrating the configuration of the gas detection device in the third modification example in the first embodiment.

FIG. 8A is a schematic sectional view illustrating a configuration of a gas detection device in a third modification example of the embodiment. FIG. 8B is a schematic top view illustrating the configuration of the gas detection device in the third modification example in the embodiment.

In the third modification example, a heating unit (heater) 60 is provided so as to heat the hydrogen absorption material film 22. Specifically, the heating unit 60 is provided on the brittle material film 21, and forms a portion of the movable film structure 20. The heating unit 60 is electrically connected to an external circuit via a lead wiring 60a. A membrane resistor or the like may be used as the heating unit 60. It is possible to allow the hydrogen absorption material film 22 to quickly release absorbed hydrogen by heating the hydrogen absorption material film 22 using the heating unit 60. As a result, it is possible to quickly return the hydrogen absorption material film 22 to a normal state by providing the heating unit 60.

Figure 9:
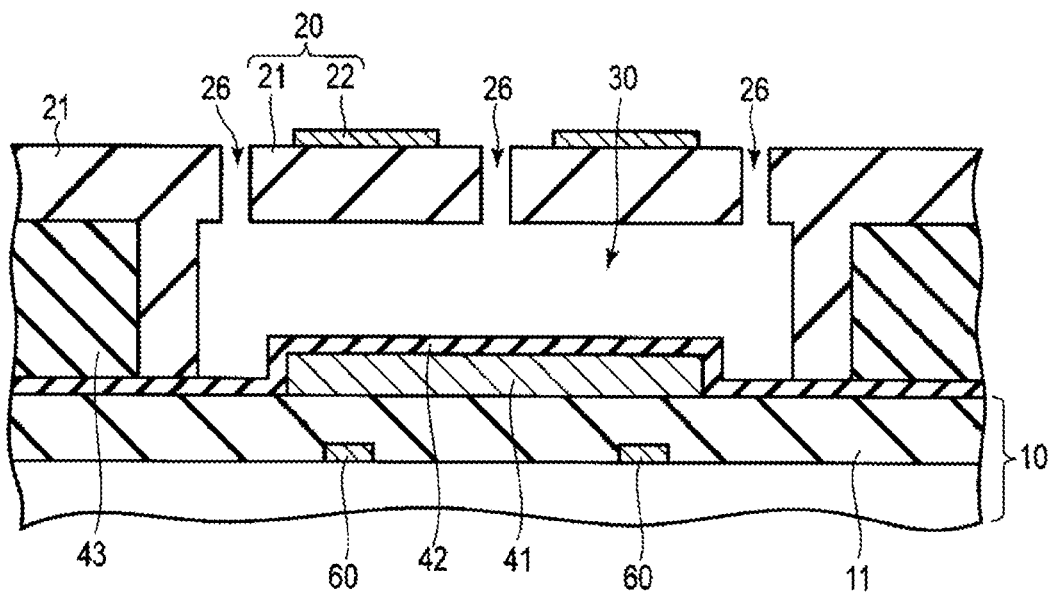
FIG. 9 is a schematic sectional view illustrating a configuration of a gas detection device in a fourth modification example of the first embodiment.

FIG. 9 is a schematic sectional view illustrating a configuration of a gas detection device in a fourth modification example of the embodiment.

Also, in the fourth modification example, similar to the third modification example, the heating unit (heater) 60 is provided is provided to heat the hydrogen absorption material film 22. Specifically, in the modification example, the heating unit 60 is provided in the substrate 10. The heating unit 60 is covered with an insulating film 11 so as to electrically insulate the heating unit 60 from the first conductive portion 41. Also, in the modification example, it is possible to allow the hydrogen absorption material film 22 to quickly release hydrogen by providing the heating unit 60.

Figure 10:
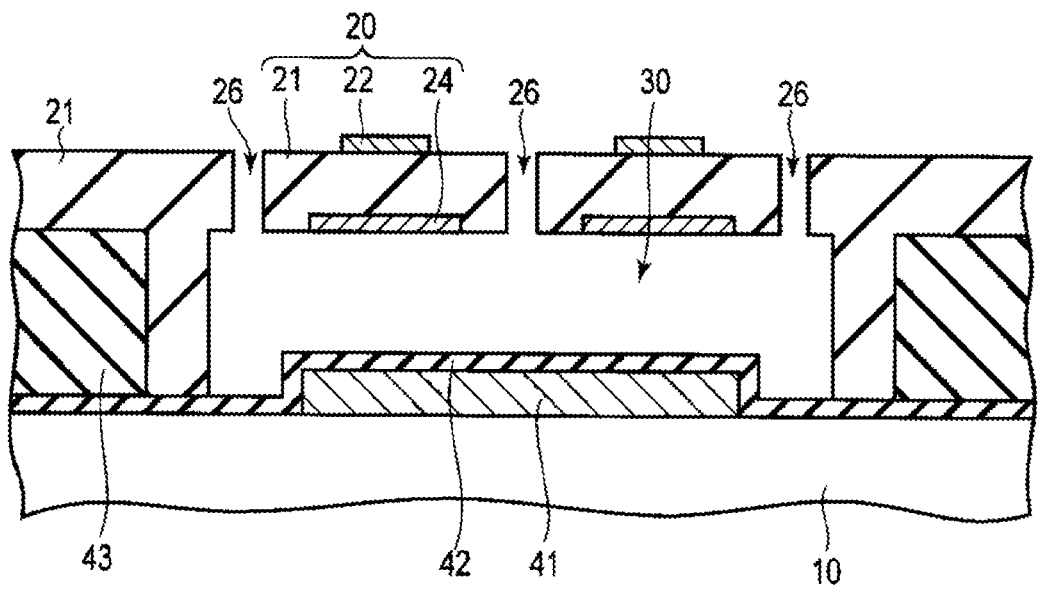
FIG. 10 is a schematic sectional view illustrating a configuration of a gas detection device in a fifth modification example in the first embodiment.
Figure 11:
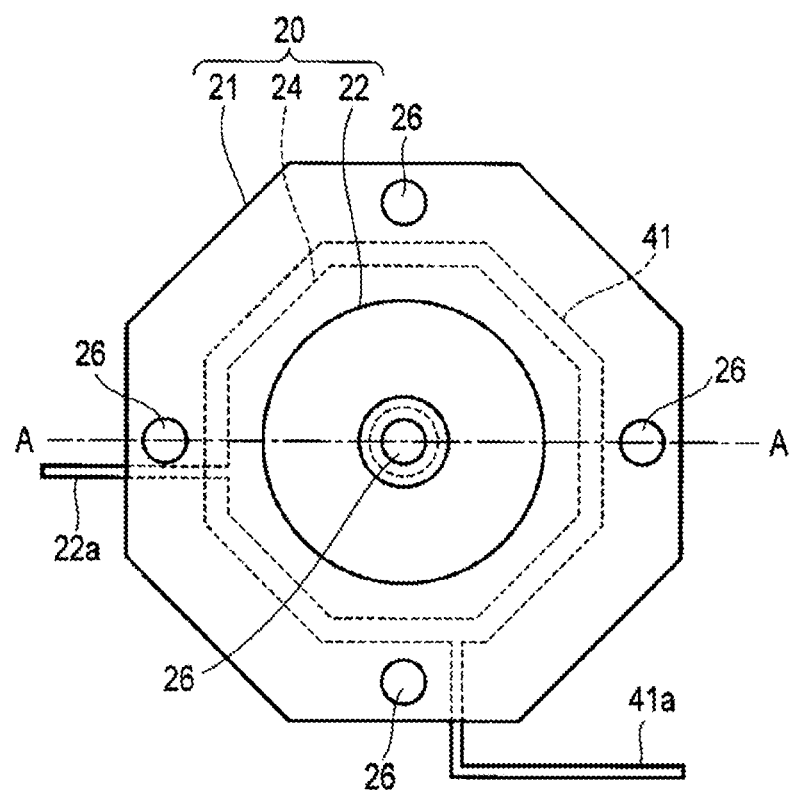
FIG. 11 is a schematic top view illustrating the configuration of the gas detection device in the fifth modification example in the first embodiment.

FIG. 10 is a schematic sectional view illustrating a configuration of a gas detection device in a fifth modification example of the embodiment. FIG. 11 is a schematic top view illustrating the configuration of the gas detection device in the fifth modification example of the embodiment.

In the fifth modification example, the movable film structure 20 further includes an electrode film 24 acting as the second electrode (upper electrode or movable electrode) of the variable capacitor. That is, in the embodiment, the hydrogen absorption material film (second film) 22 is used as the second electrode of the variable capacitor. In contrast, in the modification example, the electrode film 24 is provided separately from the hydrogen absorption material film (second film) 22, and is used as the second electrode of the variable capacitor. The electrode film 24 is electrically connected to the external circuit via a lead wiring 24a.

Also, in the modification example, if the hydrogen absorption material film 22 absorbs hydrogen, the movable film structure 20 is deformed, and the distance between the first conductive portion (lower electrode) 41 and the electrode film (upper electrode) 24 changes according to the amount of absorbed hydrogen. Therefore, similar to the embodiment, it is possible to calculate the concentration of hydrogen in the vicinity of the hydrogen absorption material film 22 based on the capacitance of the variable capacitor. In the modification example, it is possible to provide the pattern of the second electrode of the variable capacitor independently from the pattern of the hydrogen absorption material film 22 by providing the electrode film 24 separately from the hydrogen absorption material film 22. For this reason, it is possible for the size of the pattern of the second electrode (electrode film 24) to be larger than that of the pattern of the hydrogen absorption material film 22. As a result, it is possible to increase the capacitance of the variable capacitor, and to improve the sensitivity of detecting the concentration of hydrogen.

Figure 12:
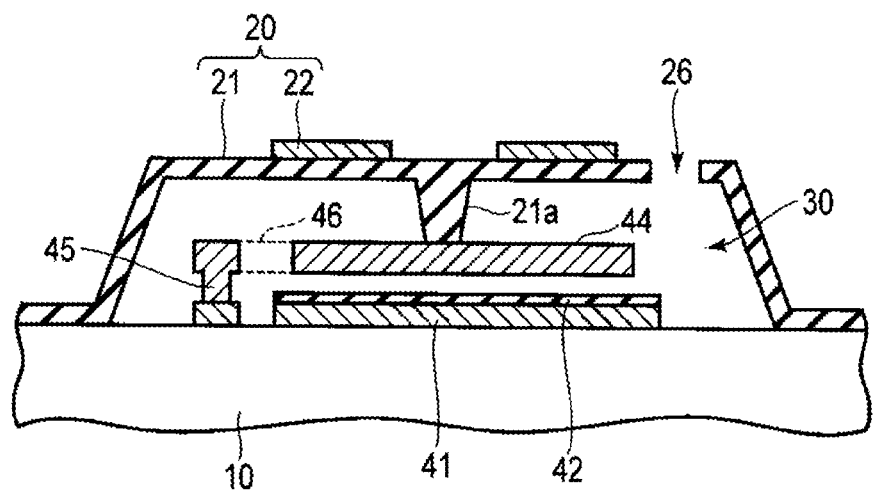
FIG. 12 is a schematic sectional view illustrating a configuration of a gas detection device in a sixth modification example of the first embodiment.
Figure 13:
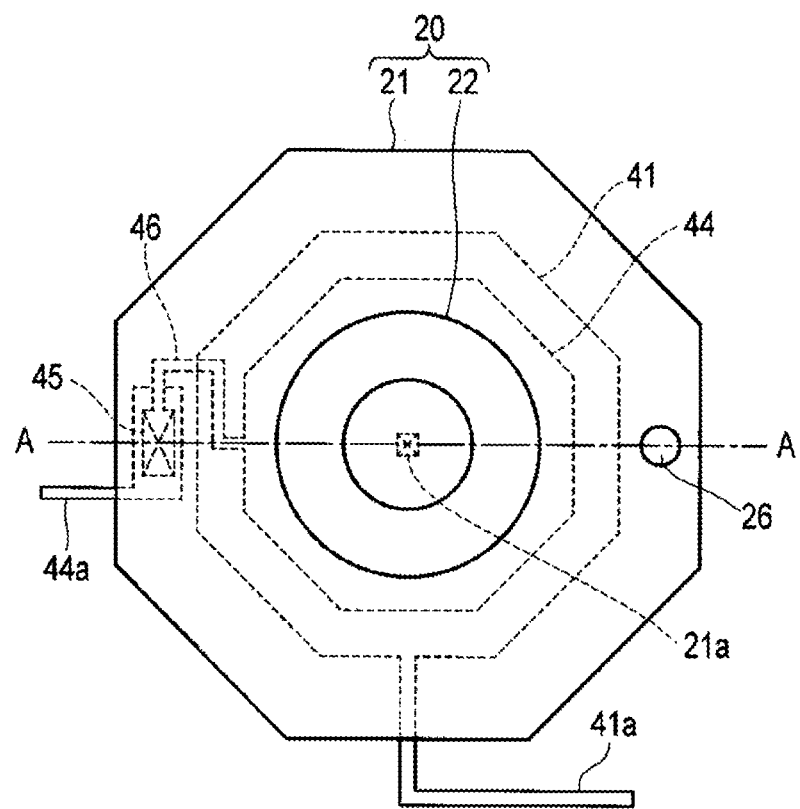
FIG. 13 is a schematic top view illustrating the configuration of the gas detection device in the sixth modification example in the first embodiment.

FIG. 12 is a schematic sectional view illustrating a configuration of a gas detection device in a sixth modification example of the embodiment. FIG. 13 is a schematic top view illustrating the configuration of the gas detection device in the sixth modification example of the embodiment.

In the sixth modification example, a second conductive portion 44 is provided such that the second conductive portion 44 is connected to the movable film structure 20 and acts as the second electrode (upper electrode or movable electrode) of the variable capacitor. That is, in the embodiment, the movable film structure 20 includes a portion acting as the second electrode of the variable capacitor. In contrast, in the sixth modification example, the second conductive portion 44 acting as the second electrode of the variable capacitor is provided separately from the movable film structure 20. The second conductive portion 44 is mechanically connected to the brittle material film 21 of the movable film structure 20 via a connection portion (anchor) 21a. The second conductive portion 44 is mechanically connected to a support portion (anchor) 45 via a spring portion 46. The second conductive portion 44 is electrically connected to the external circuit via a lead wiring 44a.

Also, in this sixth modification example, if the hydrogen absorption material film 22 absorbs hydrogen, the movable film structure 20 is deformed, and the distance between the first conductive portion (lower electrode) 41 and the second conductive portion (upper electrode) 44 changes according to the amount of absorbed hydrogen. As a result, similarly to the first embodiment, it is possible to calculate the concentration of hydrogen in the vicinity of the hydrogen absorption material film 22 based on the capacitance or change in capacitance of the variable capacitor. In addition, it is possible to increase the amount of change (the amount of change of the capacitance) of the second conductive portion (upper electrode) 44 by providing the connection portion 21a in a central portion of the movable film structure 20 in which the amount of change of the movable film structure 20 is maximized. Hence it is possible to detect the concentration of hydrogen with high accuracy.

Figure 14:
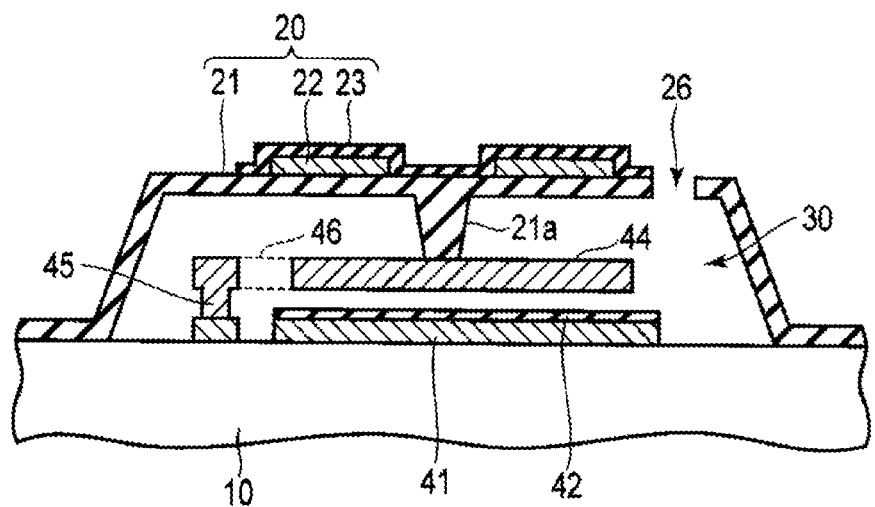
FIG. 14 is a schematic sectional view illustrating a configuration of a gas detection device in a seventh modification example of the first embodiment.

FIG. 14 is a schematic sectional view illustrating a configuration of a gas detection device in a seventh modification example of the embodiment.

Also, in the seventh modification example, similarly to the sixth modification example, the second conductive portion is provided, and acts as the second electrode (upper electrode or movable electrode) of the variable capacitor. In the modification example, similarly to the second modification example, the movable film structure 20 includes the moisture infiltration preventive film 23 covering the hydrogen absorption material film 22. As a result, in the seventh modification example, it is possible to obtain the same effects as those of the second modification example and those of the sixth modification example.

Figure 15:
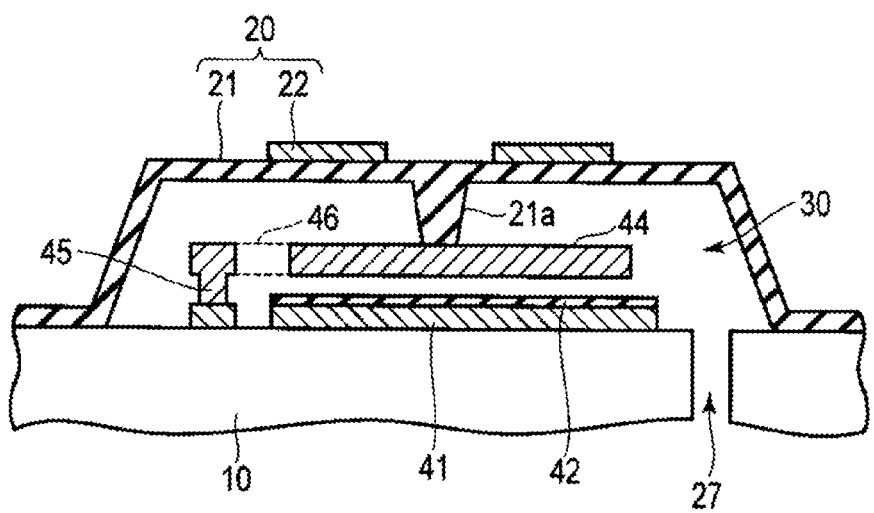
FIG. 15 is a schematic sectional view illustrating a configuration of a gas detection device in an eighth modification example of the first embodiment.

FIG. 15 is a schematic sectional view illustrating a configuration of a gas detection device in an eighth modification example of the embodiment.

In the first embodiment, the through holes 26 leading to the cavity 30 are formed in the movable film structure 20. In contrast, in the eighth modification example, the through hole 27 leading to the cavity 30 is formed in the substrate 10. As such, even if the through hole 27 is provided in the substrate 10, the inner pressure and the outer pressure of the movable film structure 20 can be kept the same. Through holes may also be provided in both the movable film structure 20 and the substrate 10.

The configuration of the first embodiment and the configurations of the first to eighth modification examples thereof may be suitably combined together.

FIGS. 16 to 19 are schematic views illustrating various patterns (planar patterns) of the hydrogen absorption material film 22.

Figure 16:
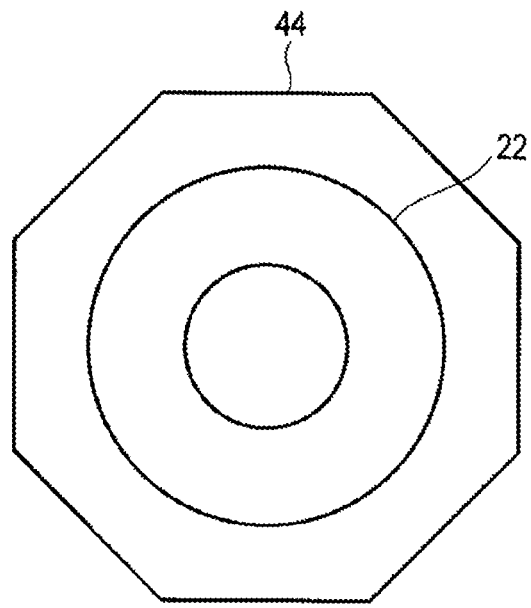
FIG. 16 is a schematic view illustrating an example of the pattern of a hydrogen absorption material film in the first embodiment.

In FIG. 16, the hydrogen absorption material film 22 has a donut-shaped pattern, i.e., an annular pattern. As described above, if the hydrogen absorption material film 22 absorbs hydrogen, the hydrogen absorption material film 22 expands. For this reason, the movable film structure 20 is bent due to stress. If the movable film structure 20 is bent upwardly, the distance between the upper electrode and the lower electrode of the variable capacitor increases. Therefore, the capacitance of the variable capacitor decreases. As a result, hydrogen detection sensitivity deteriorates. In contrast, if the movable film structure 20 is bent downwardly, the distance between the upper electrode and the lower electrode of the variable capacitor decreases. Therefore, the capacitance of the variable capacitor decreases, and hydrogen detection sensitivity improves. As illustrated in FIG. 16, if the hydrogen absorption material film 22 has a donut-shaped pattern and if the hydrogen absorption material film 22 is formed on the upper surface of the brittle material film 21, the hydrogen absorption material film 22 bends the movable film structure 20 downwardly when the hydrogen absorption material film 22 absorbs hydrogen and expands. As a result, as illustrated in FIG. 16, if the hydrogen absorption material film 22 has a donut-shaped pattern, it is possible to improve hydrogen detection sensitivity by forming the hydrogen absorption material film 22 on the upper surface of the brittle material film 21.

Figure 17:
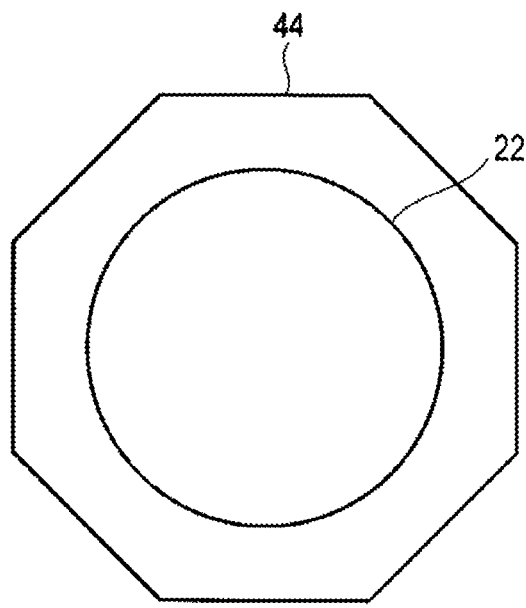
FIG. 17 is a schematic view illustrating another example of the pattern of the hydrogen absorption material film in the first embodiment.

In FIG. 17, the hydrogen absorption material film 22 has a disc-shaped pattern. As illustrated in FIG. 17, if the hydrogen absorption material film 22 has a disc-shaped pattern and if the hydrogen absorption material film 22 is formed on the lower surface of the brittle material film 21, hydrogen absorption of the hydrogen absorption material film 22 bends the movable film structure 20 downwardly. As a result, if the hydrogen absorption material film 22 has a disc-shaped pattern as illustrated in FIG. 17, it is possible to improve hydrogen detection sensitivity by forming the hydrogen absorption material film 22 on the lower surface of the brittle material film 21.

Since the hydrogen absorption material films 22 in FIGS. 16 and 17 are formed into one large pattern, it is possible to increase the amount of the physical size change of the hydrogen absorption material film 22. For this reason, it is possible to considerably change the capacitance of the variable capacitor, and to improve the hydrogen detection sensitivity.

Figure 18:
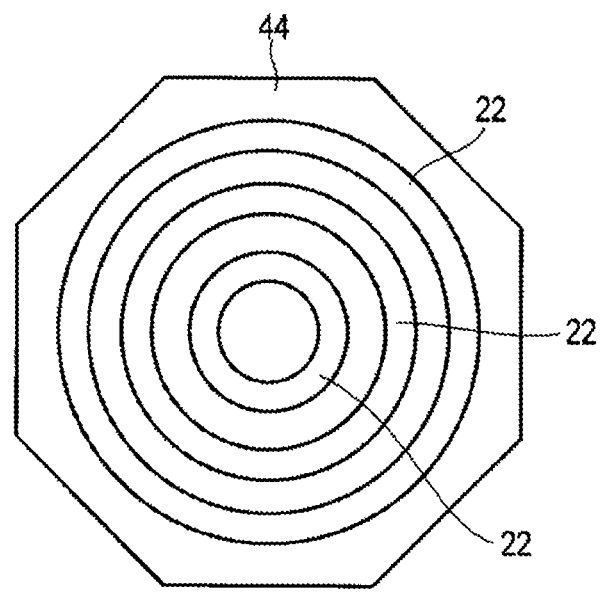
FIG. 18 is a schematic view illustrating a still another example of the pattern of the hydrogen absorption material film in the first embodiment.
Figure 19:
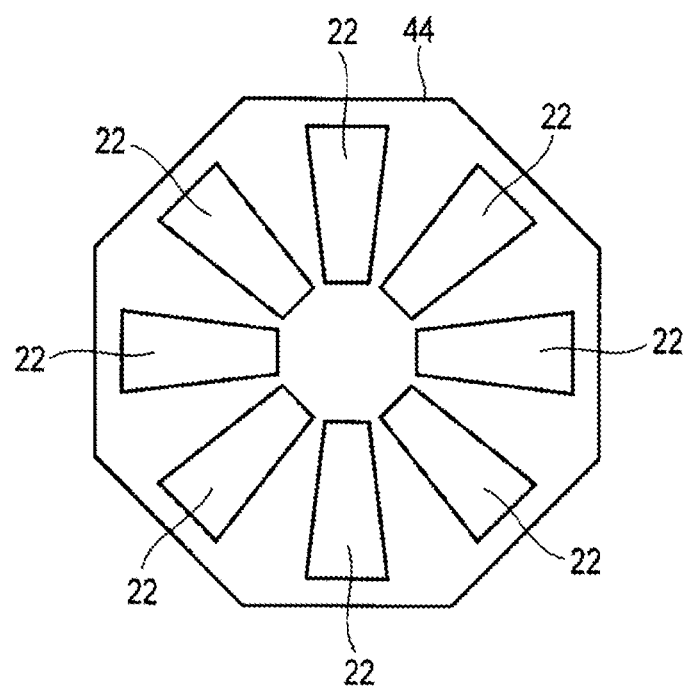
FIG. 19 is a schematic view illustrating a still another example of the pattern of the hydrogen absorption material film in the first embodiment.

In FIG. 18, the hydrogen absorption material film 22 has a concentric circular pattern. In FIG. 19, the hydrogen absorption material film 22 has a radial pattern. As described above, if the hydrogen absorption material film 22 absorbs hydrogen and expands, a high stress is applied to the hydrogen absorption material film 22. As a result, buckling or the like may occur, which is a problem. As illustrated in FIGS. 18 and 19, if the pattern of the hydrogen absorption material film 22 is divided into multiple portions, it is possible to reduce stress, and to improve reliability of the movable film structure 20.

The hydrogen absorption material film 22 may have patterns other than the patterns illustrated in FIGS. 16 to 19.

Figure 20:
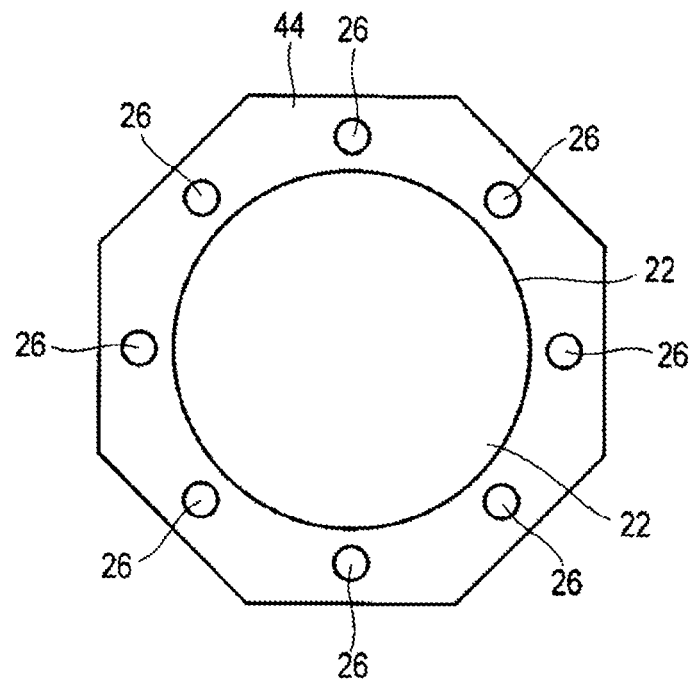
FIG. 20 is a schematic view illustrating an example of the pattern of through holes in the first embodiment.
Figure 21:
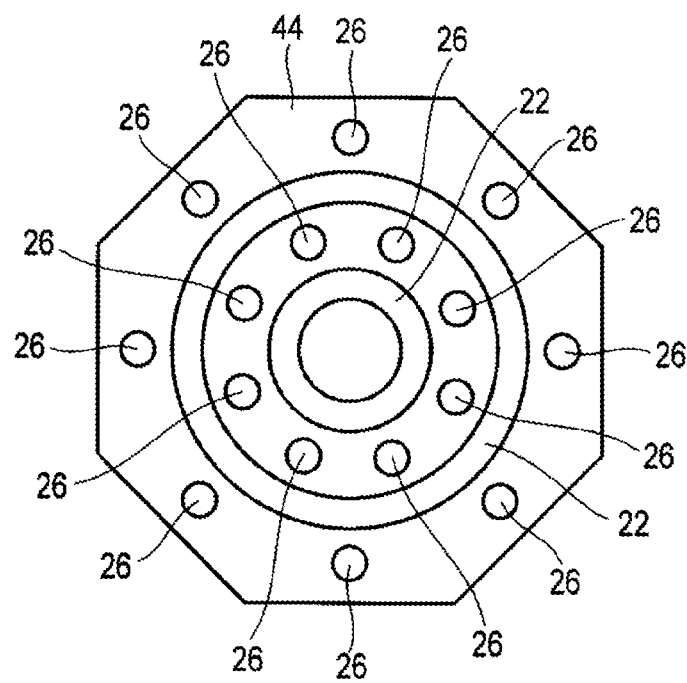
FIG. 21 is a schematic view illustrating an example of the pattern of through holes in the first embodiment.

FIGS. 20 and 21 are schematic views illustrating the pattern (planar pattern) of the through holes 26.

In the pattern illustrated in FIG. 20, the multiple through holes 26 are provided on a single concentric circle. In the pattern illustrated in FIG. 21, the multiple through holes 26 are respectively provided on multiple concentric circles. The through holes 26 may have patterns other than the patterns illustrated in FIGS. 20 and 21.

FIGS. 22 to 27 are schematic sectional views illustrating an example of a method of manufacturing the gas detection device of the embodiment.

Figure 22:
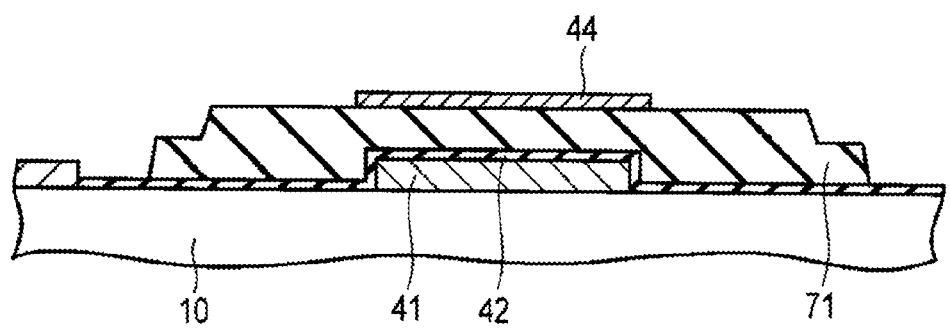
FIG. 22 is a schematic sectional view illustrating a portion of a method of manufacturing the gas detection device of the first embodiment.

First, as illustrated in FIG. 22, the first conductive portion 41 acting as the first electrode (lower electrode or fixed electrode) of the variable capacitor is formed on the substrate 10. Subsequently, the insulating film 42 is formed so as to cover the first conductive portion 41 and the substrate 10. Subsequently, a first sacrificial layer 71 is formed so as to cover the first conductive portion 41. The second conductive portion 44 acting as the second electrode (upper electrode or movable electrode) of the variable capacitor is formed on the first sacrificial layer 71.

Figure 23:
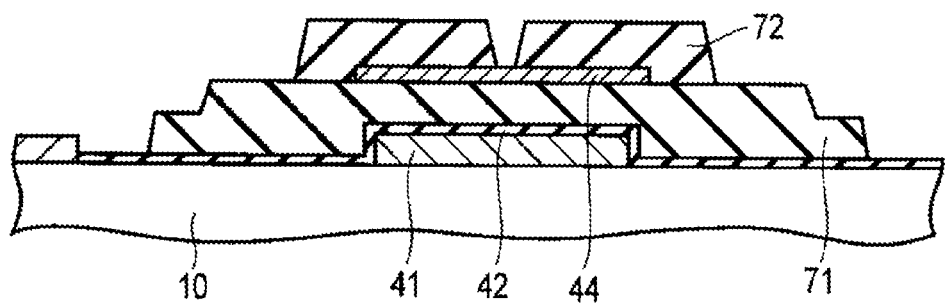
FIG. 23 is a schematic sectional view illustrating a portion of the method of manufacturing the gas detection device of the first embodiment.

Subsequently, as illustrated in FIG. 23, a second sacrificial layer 72 is formed so as to cover the second conductive portion 44. An opening leading to the second conductive portion 44 is formed in the second sacrifice layer 72 via patterning.

Figure 24:
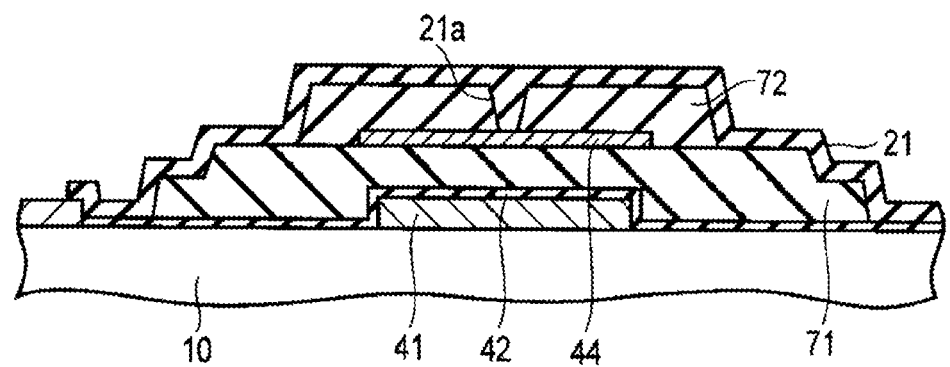
FIG. 24 is a schematic sectional view illustrating a portion of the method of manufacturing the gas detection device of the first embodiment.

Subsequently, as illustrated in FIG. 24, the brittle material film 21 is formed so as to cover the first sacrificial layer 71 and the second sacrificial layer 72. At this time, the opening formed in the second sacrificial layer 72 is filled with a brittle material, and the connection portion 21a is formed.

Figure 25:
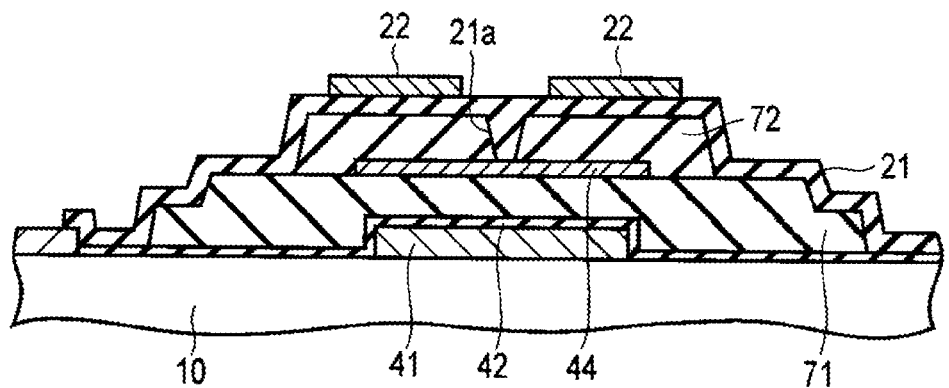
FIG. 25 is a schematic sectional view illustrating a portion of the method of manufacturing the gas detection device of the first embodiment.

Subsequently, as illustrated in FIG. 25, the hydrogen absorption material film 22 pattern is formed on the brittle material film 21.

Figure 26:
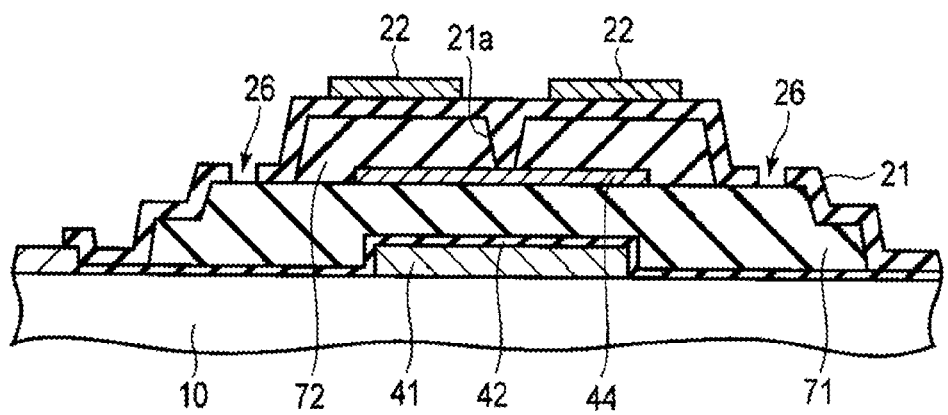
FIG. 26 is a schematic sectional view illustrating a portion of the method of manufacturing the gas detection device of the first embodiment.

Subsequently, as illustrated in FIG. 26, multiple through holes (vent holes) 26 are formed in the brittle material film 21.

Figure 27:
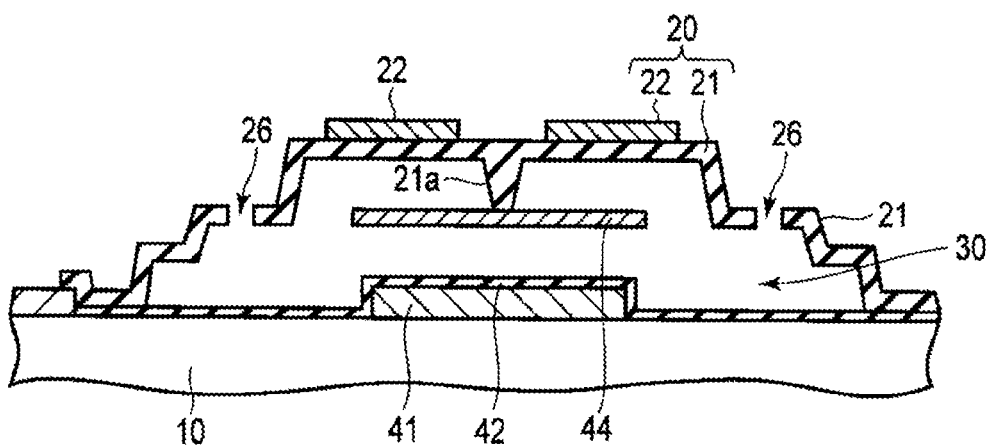
FIG. 27 is a schematic sectional view illustrating a portion of the method of manufacturing the gas detection device of the first embodiment.

Subsequently, as illustrated in FIG. 27, etching gas is supplied via the through holes 26, and the first sacrificial layer 71 and the second sacrificial layer 72 are removed. As a result, the movable film structure 20 including the brittle material film 21 and the hydrogen absorption material film 22 is obtained, and the cavity 30 is formed inside the movable film structure 20.

According to the aforementioned manufacturing method, the through holes 26 used to remove the first sacrificial layer 71 and the second sacrifice layer 72 may be used as the through holes 26 through which the inner pressure and the outer pressure of the movable film structure 20 are kept the same. As a result, it is possible to efficiently manufacture the gas detection device using the aforementioned manufacturing method.

Embodiment 2

Hereinafter, a gas detection device of a second embodiment will be described. Since the basic configuration is the same as that of the first embodiment, description of the items described in the first embodiment will be omitted. Similarly to the first embodiment, the gas detection device of the embodiment is used as a hydrogen gas detection device, and is manufactured using MEMS process technology.

Figure 28:
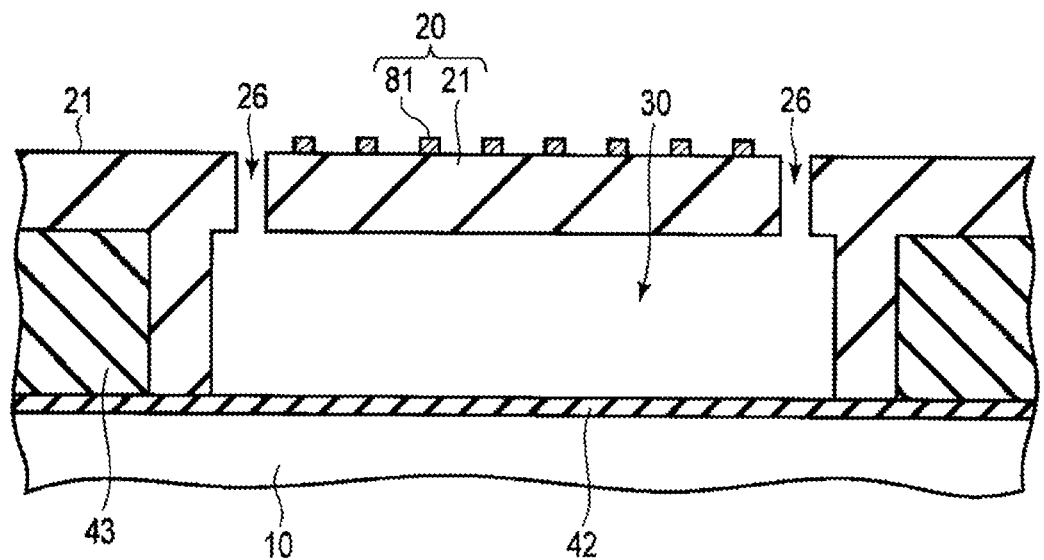
FIG. 28 is a schematic sectional view illustrating a configuration of a gas detection device of a second embodiment.
Figure 29:
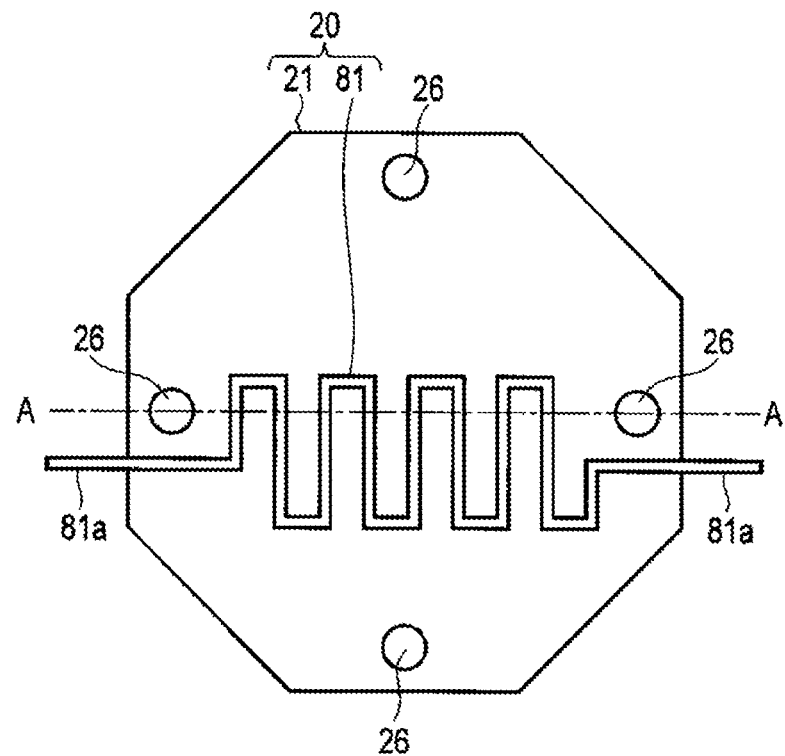
FIG. 29 is a schematic top view illustrating the configuration of the gas detection device of the second embodiment.

FIG. 28 is a schematic sectional view illustrating a configuration of the gas detection device (hydrogen gas detection device) of the embodiment. FIG. 29 is a schematic top view illustrating the configuration of the gas detection device (hydrogen gas detection device) of the embodiment.

The gas detection device illustrated in FIGS. 28 and 29 includes the substrate 10, and the movable film structure 20 provided on the substrate 10. The cavity 30 is formed inside the movable film structure 20.

Similarly to the first embodiment, the substrate 10 contains a circuit area containing a semiconductor substrate (for example, silicon substrate), a MOS transistor, wirings, and the like.

The movable film structure 20 includes the brittle material film (first film) 21 formed of a brittle material, and a hydrogen absorption material film (second film) 81 formed of a hydrogen absorbing material (hydrogen storage material). In the embodiment, the hydrogen absorption material film 81 is provided on the upper surface of the brittle material film 21. In the embodiment, the hydrogen absorption material film 81 acts as a variable resistor, and is electrically connected to an external circuit via a lead wiring 81a. The movable film structure 20 includes the multiple through holes (vent holes) 26 which lead to the cavity 30. Specifically, the multiple through holes 26 are formed in and extend through the brittle material film 21. The inner pressure and the outer pressure of the movable film structure 20 are kept the same via the through holes 26.

Similar to the first embodiment, the brittle material film (first film) 21 acts as a base film of the movable film structure 20. Similarly to the first embodiment, the brittle material film 21 is preferably formed of a material containing silicon (Si). The specific material of the brittle material film 21 is the same as that of the first embodiment. In the embodiment, since the hydrogen absorption material film 81 acting as a variable resistor is formed on the brittle material film 21, an insulating material is preferably used as the material of the brittle material film 21. In the embodiment, a silicon nitride film (SiN film) is used as the brittle material film 21.

Similarly to the first embodiment, the hydrogen absorption material film 81 (hydrogen storage material film or second film) acts as a hydrogen detection film. The specific material of the hydrogen absorption material film 81 is the same as that of the hydrogen absorption material film 22 of the first embodiment. In the embodiment, a palladium film (Pd film) or a palladium alloy film (Pd alloy film) is used as the hydrogen absorption material film 81. Since the hydrogen absorption material film 81 is used as a variable resistor, the entire length of the hydrogen absorption material film 81 is increased by providing multiple bent portions.

If the hydrogen absorption material film 81 absorbs (stores) hydrogen, the hydrogen absorption material film 81 expands, and the resistance of the hydrogen absorption material film 81 changes. For this reason, the resistance value of the hydrogen absorption material film 81 changes according to the amount of absorbed hydrogen. As a result, it is possible to calculate the amount of absorbed hydrogen by obtaining the resistance value of the hydrogen absorption material film 81. That is, it is possible to calculate the concentration of hydrogen in the vicinity of the hydrogen absorption material film 81 by obtaining the resistance value of the hydrogen absorption material film 81.

Since the hydrogen absorption material film 81 expands when absorbing hydrogen, if the base film of the movable film structure 20 is fixed, a high stress is applied to the hydrogen absorption material film 81 along with the absorption of hydrogen. In the embodiment, the cavity 30 is provided inside of the movable film structure 20, and the movable film structure 20 is capable of moving. For this reason, when the hydrogen absorption material film 81 expands, the base film is deformed, and thus, it is possible to reduce stress applied to the hydrogen absorption material film 81.

Also, in the embodiment, since the brittle material film 21 is used as the base film (brittle material film 21) of the movable film structure 20, there is almost no deformation of the base film which is caused by creep fatigue or the like. If the base film of the movable film structure 20 is permanently deformed, the resistance or stress of the hydrogen absorption material film 81 may change due to this deformation of the hydrogen absorption material film 81, which is a problem. In the embodiment, since there is almost no permanent deformation of the base film, the resistance or stress of the hydrogen absorption material film 81 may not change due to this deformation of the hydrogen absorption material film 81. Therefore, it is possible to reliably detect a change in the resistance or stress of the hydrogen absorption material film 81 based on the absorption of hydrogen. As a result, in the embodiment, it is possible to detect the concentration of hydrogen with high accuracy, and to obtain a high-performance gas detection device (hydrogen gas detection device) having good detection accuracy and good reliability.

In the embodiment, since the multiple through holes 26 leading to the cavity 30 are provided in the movable film structure 20, it is possible to keep the inner pressure and the outer pressure of the movable film structure 20 to be the same, and it is possible to prevent a pressure difference from causing deformation of the movable film structure 20. As a result, in the embodiment, it is possible to reliably detect a change in the resistance of the hydrogen absorption material film 81 based on the absorption of hydrogen, and it is possible to accurately detect the concentration of hydrogen.

Figure 30:
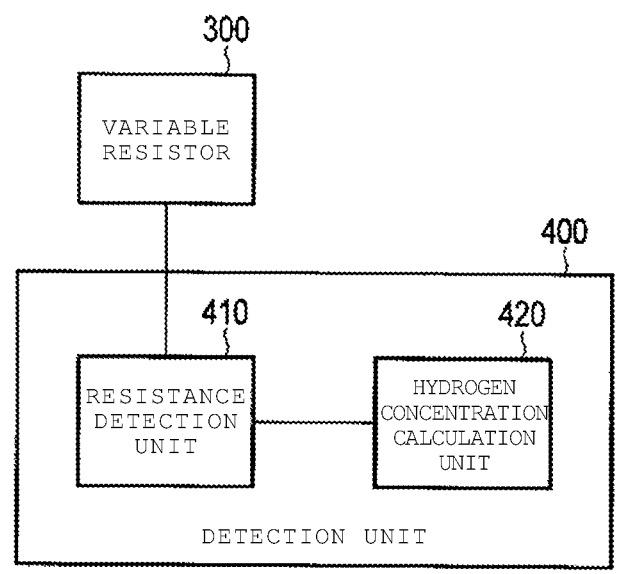
FIG. 30 is a block diagram illustrating the entire configuration of the gas detection device of the second embodiment.

FIG. 30 is a block diagram illustrating the entire configuration of the gas detection device (hydrogen gas detection device) of the embodiment. As illustrated in FIG. 30, a detection unit 400 is connected to a variable resistor 300 having the aforementioned structure. The detection unit 400 may be provided in the substrate 10 illustrated in FIG. 28, or may be provided remotely from the substrate 10. The detection unit 400 includes a resistance detection unit 410 that detects the resistance value of the variable resistor 300, and a hydrogen concentration calculation unit 420 that calculates the concentration of hydrogen based on the resistance value detected by the resistance detection unit 410. It is possible to calculate the concentration of hydrogen with high accuracy via the hydrogen concentration calculation unit 420 by obtaining a relationship between the resistance value of the variable resistor and the concentration of hydrogen in advance.

Figure 31:
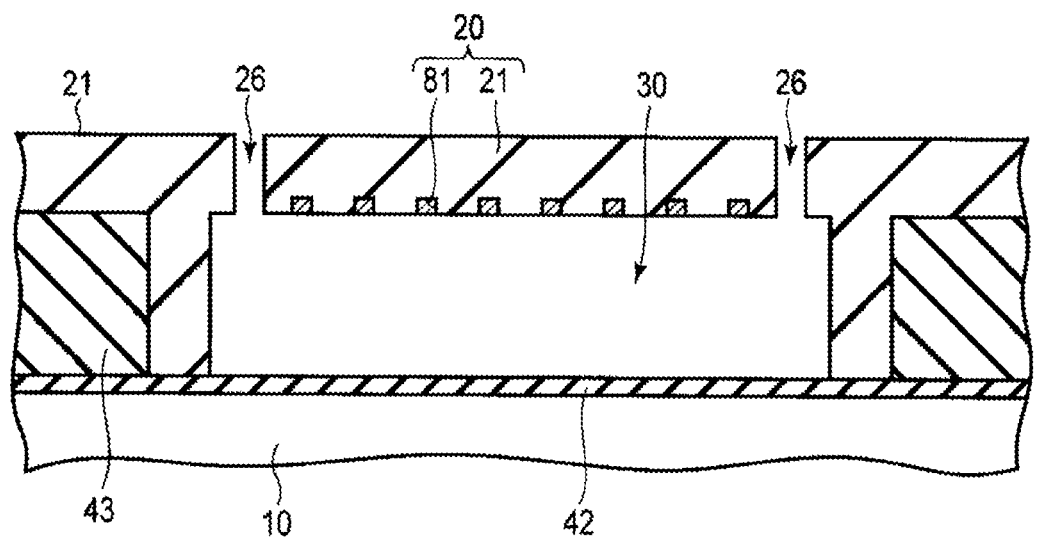
FIG. 31 is a schematic sectional view illustrating a configuration of a gas detection device in a modification example of the second embodiment.

FIG. 31 is a schematic sectional view illustrating a configuration of a gas detection device (hydrogen gas detection device) in a modification example of the embodiment. In the embodiment, the hydrogen absorption material film 81 is provided on the upper surface of the brittle material film 21. In contrast, in the modification example, the hydrogen absorption material film 81 is provided on the lower surface of the brittle material film 21. The rest of the basic configuration is the same as that of the embodiment. Also, in this configuration, it is possible to obtain the same effects as those of the embodiment.

Also, in the embodiment, it is possible to suitably adopt the same configurations as various configurations described in the first embodiment and the modification examples of the first embodiment.

Embodiment 3

Hereinafter, a gas detection device of a third embodiment will be described. Since the basic configuration is the same as that of the first embodiment, description of the items described in the first embodiment will be omitted. Similar to the first embodiment, the gas detection device of the embodiment is used as a hydrogen gas detection device, and is manufactured using MEMS process technology.

Figure 32:
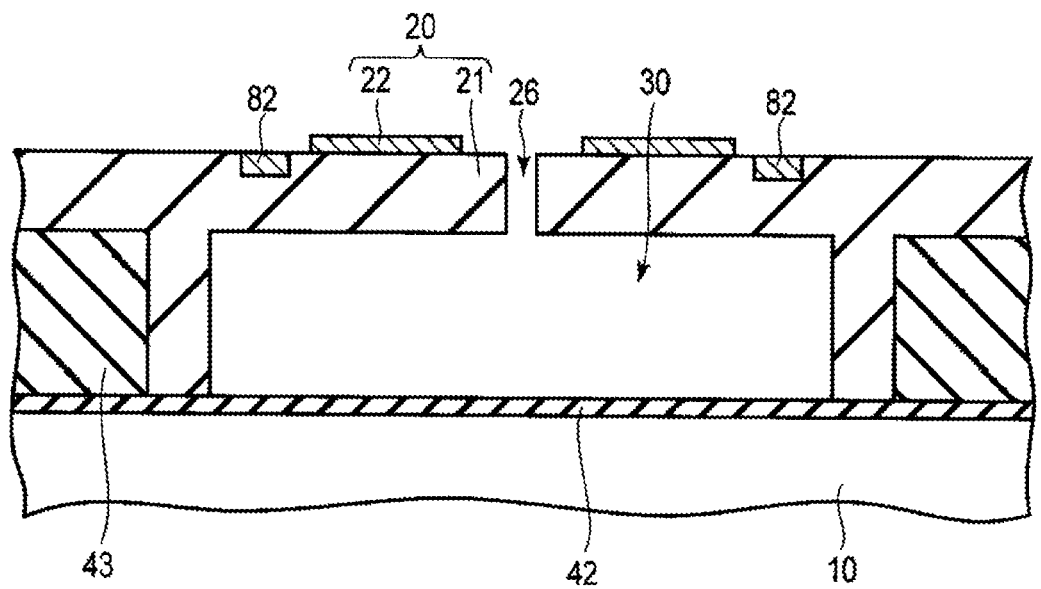
FIG. 32 is a schematic sectional view illustrating a configuration of a gas detection device of a third embodiment.
Figure 33:
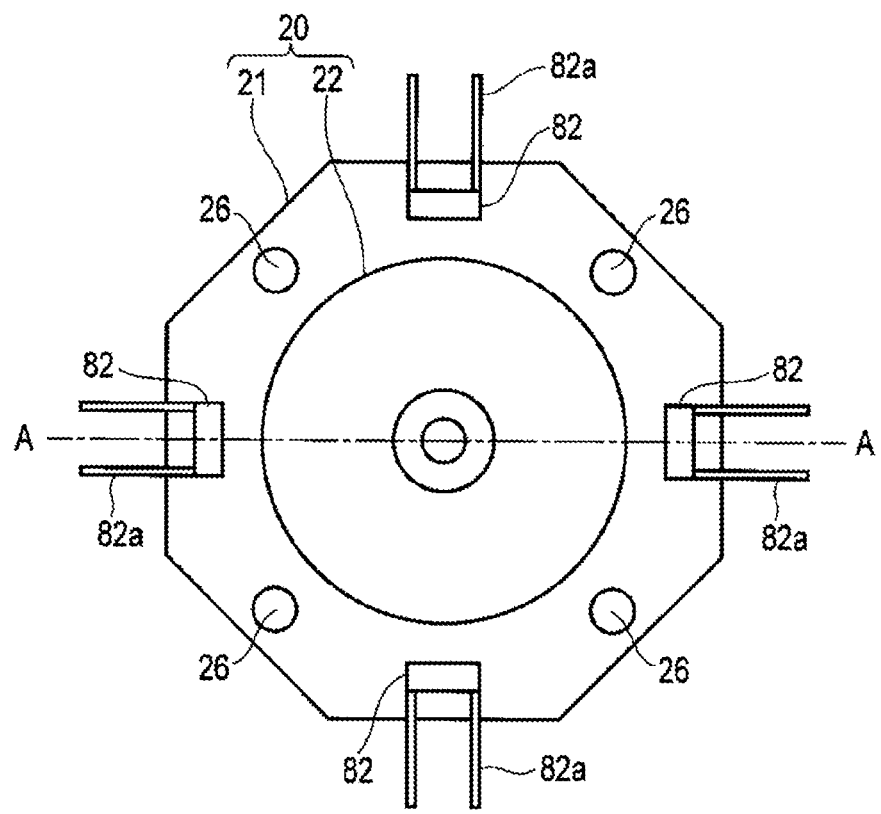
FIG. 33 is a schematic top view illustrating the configuration of the gas detection device of the third embodiment.

FIG. 32 is a schematic sectional view illustrating a configuration of the gas detection device (hydrogen gas detection device) of the embodiment. FIG. 33 is a schematic top view illustrating the configuration of the gas detection device (hydrogen gas detection device) of the embodiment. The gas detection device illustrated in FIGS. 32 and 33 includes the substrate 10, and the movable film structure 20 provided on the substrate 10. The cavity 30 is formed inside the movable film structure 20.

Similarly to the first embodiment, the substrate 10 contains a circuit area containing a semiconductor substrate (for example, silicon substrate), and a MOS transistor, wirings, and the like.

The movable film structure 20 includes the brittle material film (first film) 21 formed of a brittle material, and the hydrogen absorption material film (second film) 22 formed of a hydrogen absorption material (hydrogen storage material). In the configuration illustrated in FIGS. 32 and 33, the hydrogen absorption material film 22 is provided on the upper surface of the brittle material film 21. Alternatively, the hydrogen absorption material film 22 may be provided on the lower surface of the brittle material film 21. In the embodiment, a piezoresistive portion 82 is provided in a portion of the movable film structure 20. The piezoresistive portion 82 is electrically connected to an external circuit via a lead wiring 82a. Silicon (Si), silicon-germanium (SiGe), or the like may be used as the material of the piezoresistive portion 82. The movable film structure 20 includes the multiple through holes (vent holes) 26 which lead to the cavity 30. Specifically, the multiple through holes 26 are provided in and through the brittle material film 21. The inner pressure and the outer pressure of the movable film structure 20 are kept the same by communication through the through holes 26.

As described above, if the hydrogen absorption material film 22 absorbs (stores) hydrogen, the hydrogen absorption material film 22 expands (the volume increases). For this reason, if the hydrogen absorption material film 22 absorbs hydrogen, the movable film structure 20 is deformed, and stress applied to the piezoresistive portion 82 changes. Since the amount of expansion of the hydrogen absorption material film 22 changes according to the amount of absorbed hydrogen, stress applied to the piezoresistive portion 82 also changes according to the amount of absorbed hydrogen, and the resistance of the piezoresistive portion 82 changes according to stress. As a result, it is possible to calculate the amount of absorbed hydrogen by obtaining the resistance value of the piezoresistive portion 82. That is, it is possible to calculate the concentration of hydrogen in the vicinity of the hydrogen absorption material film 22 by obtaining the resistance value of the piezoresistive portion 82.

Also, in the embodiment, since the brittle material film 21 is used as the base film of the movable film structure 20, there is almost no permanent deformation of the base film which is caused by creep fatigue or the like. For this reason, in the embodiment, it is possible to reliably detect a change in the resistance of the piezoresistive portion 82 based on deformation of the hydrogen absorption material film 22. As a result, in the embodiment, it is possible to detect the concentration of hydrogen with high accuracy based on a change in the resistance of the piezoresistive portion 82, and it is possible to obtain a high-performance gas detection device (hydrogen gas detection device) having good detection accuracy and good reliability.

In the embodiment, since the multiple through holes 26 leading to the cavity 30 are provided in the movable film structure 20, it is possible to keep the inner pressure and the outer pressure of the movable film structure 20 the same, and it is possible to prevent a pressure difference from causing deformation of the movable film structure 20. As a result, in the embodiment, it is possible to reliably detect a change in the resistance of the piezoresistive portion 82 based on the absorption of hydrogen, and it is possible to accurately detect the concentration of hydrogen.

The entire configuration of the gas detection device (hydrogen gas detection device) of the embodiment is the same as the configuration of the second embodiment illustrated in the block diagram of FIG. 30. As a result, also, in the embodiment, it is possible to detect the concentration of hydrogen similar to that of the second embodiment illustrated in FIG. 30.

Also, in the embodiment, it is possible to suitably adopt the same configurations as various configurations described in the first embodiment and the modification examples of the first embodiment.

In the first, second, and third embodiments, the planar pattern of an inner area (corresponding to the cavity 30) of the movable film structure 20, which is defined by the brittle material film 21, is a regular octagon. Alternatively, the planar pattern may be a regular n-polygon (n is an integer equal to or greater than three, and preferably is an integer equal to or greater than four) such as a regular tetragon or a regular hexagon, or a circle. More typically, the planar pattern of the inner area of the movable film structure 20 preferably is a shape with rotational symmetry of the n-th order (n is an integer equal to or greater than three, and preferably is an integer equal to or greater than four). Similarly, the planar pattern of the hydrogen absorption material film 22 preferably is a shape with rotational symmetry of the n-th (n is an integer equal to or greater than three, and preferably is an integer equal to or greater than four) order.

Embodiment 4

Hereinafter, a gas detection device of a fourth embodiment will be described. Since the basic configuration is similar to that of the first embodiment, description of the items described in the first embodiment will be omitted. Similar to the first embodiment, the gas detection device of the embodiment is also manufactured via MEMS process technology. The gas detection device of the embodiment may be used as a detection device that detects predetermined gases such as a hydrogen gas, water vapor, and a volatile organic compound gas.

Figure 34:
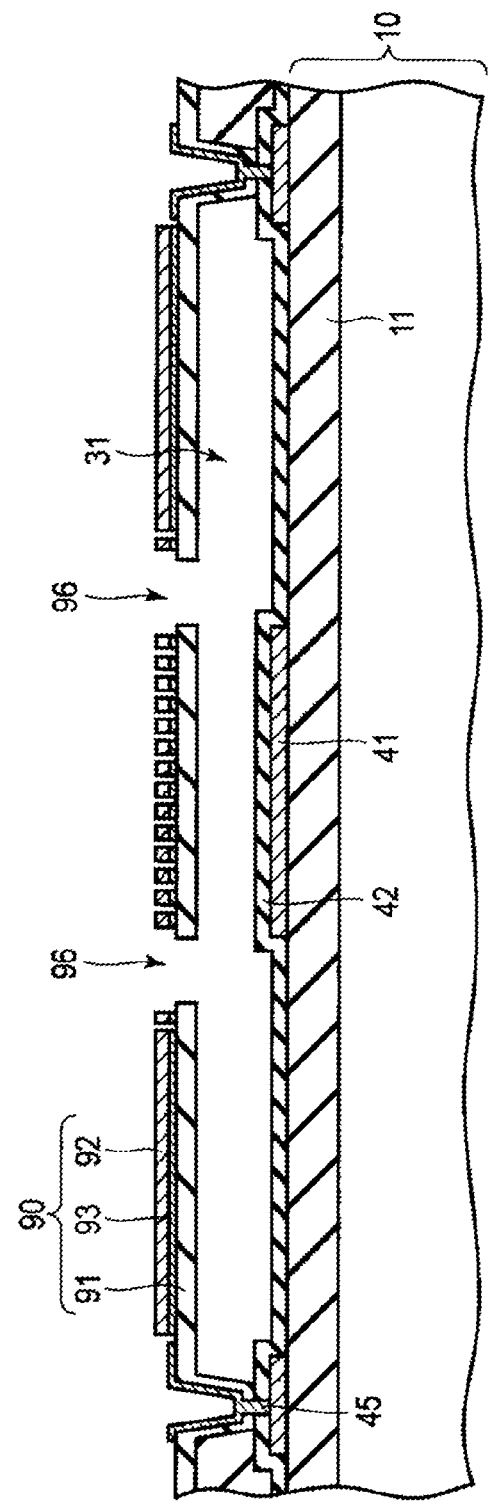
FIG. 34 is a schematic sectional view illustrating a configuration of a gas detection device of a fourth embodiment.
Figure 35:
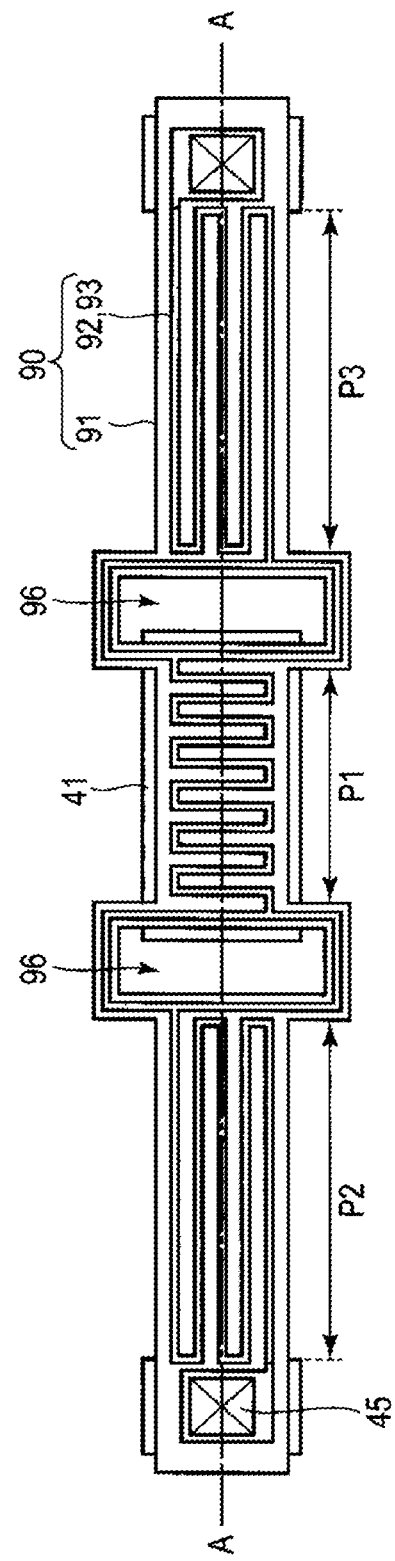
FIG. 35 is a schematic top view illustrating the configuration of the gas detection device of the fourth embodiment.

FIG. 34 is a schematic sectional view illustrating a configuration of the gas detection device of the embodiment. FIG. 35 is a schematic top view illustrating the configuration of the gas detection device of the embodiment. A section taken along line A-A in FIG. 35 substantially corresponds to FIG. 34.

The gas detection device illustrated in FIGS. 34 and 35 includes the substrate 10, and a movable film structure 90 provided on the substrate 10. A gap (air gap or the like) 31 is formed inside the movable film structure 90.

Similarly to the first embodiment, the substrate 10 contains a circuit area containing a semiconductor substrate (for example, a silicon substrate), a MOS transistor, wirings, and the like. The insulating film (SiO film, SiN film, or the like) 11 is formed on a surface of the semiconductor substrate.

The movable film structure 90 includes an insulating material film (first film) 91 formed of an insulating material; a gas sensitive film (second film) 92 that is deformed when absorbing or adsorbing a predetermined gas; and a resistive film (third film) 93 that acts as a resistor for a heater. The insulating material film (first film) 91 is in contact with the resistive film (third film) 93. The gas sensitive film (second film) 92 is in contact with the resistive film (third film) 93, such that the resistive film (third film) 93 is between the insulating material film (first film) 91 and the gas sensitive film (second film) 92. The gap 31 is provided between the substrate 10 and the movable film structure 90. Multiple through holes 96 are formed in and through the movable film structure 90 and communicate with the gap 31.

The insulating material film (first film) 91 acts as a base film of the movable film structure 90. The insulating material film 91 is preferably formed of a brittle material. The same brittle material as that of the brittle material film 21 of the first embodiment may be used as the material of the insulating material film 91. In the embodiment, a SiN film, a SiO film, an AlO film, or the like may be used as the insulating material film 91.

The gas sensitive film (second film) 92 acts as a gas detection film that detects a predetermined gas. Examples of the predetermined gas include hydrogen gas, water vapor, and volatile organic compound gas. If a hydrogen gas is detected as the predetermined gas, a hydrogen absorption material film (hydrogen storage material film) is used as the gas sensitive film 92. The same material as that of the hydrogen absorption material film 22 of the first embodiment may be used as the material of the hydrogen absorption material film. If water vapor is detected as the predetermined gas, the gas sensitive film 92 may be formed of polyimide. If a volatile organic compound gas is detected as the predetermined gas, the gas sensitive film 92 may be formed of polystyrene sulfonate (PSS), dextran, polyvinylpyrrolidone (PVP), carboxymethyl cellulose (CMC), or the like. Either a conductive material or an insulating material may be used as the material of the gas sensitive film 92. In the embodiment, a conductive material is used as the material of the gas sensitive film 92.

The resistive film (third film) 93 acts as a resistor to form a resistive heater. That is, if current flows through the resistive film 93, the resistive film 93 generates heat. Therefore, the resistive film 93 acts as a heater. Ti, Ni, Cu, Pd, Pt, Pd—Ni, or the like may be used as the material of the resistive film 93. The resistive film 93 is used to separate the predetermined gas, which is absorbed or adsorbed by the gas sensitive film 92, from the gas sensitive film 92. That is, the temperature of the gas sensitive film 92 is increased by heat generated by the resistive film 93, and thus, it is possible to separate, i.e., outgas, the predetermined gas from the gas sensitive film 92. In order to use the resistive film 93 as a resistor for a heater, the resistive film 93 is formed into a wire-like wiring pattern, and the entire length of the resistive film 93 is increased by providing multiple bent portions in the resistive film 93. The resistive film 93 also acts as a second electrode (upper electrode or movable electrode) of a variable capacitor.

The first conductive portion 41 acting as a first electrode (lower electrode or fixed electrode) of the variable capacitor is provided on the substrate 10. The first conductive portion 41 faces the resistive film 93 that acts as the second electrode (upper electrode or movable electrode) of the variable capacitor. Al, W, Ni, Ti, Cu, Au, or the like may be used as the material of the first conductive portion 41. The first conductive portion 41 and the substrate 10 are covered with the insulating film (SiN film, SiO film, AlO film, or the like) 42.

When viewed from a direction perpendicular to a main surface of the substrate 10, that is, when viewed from a direction perpendicular to a main surface of the movable film structure 90, at least a portion of the pattern of the gas sensitive film (second film) 92 overlaps at least a portion of the pattern of the resistive film (third film) 93. In the embodiment, when viewed from the direction perpendicular to the main surface of the substrate 10, the pattern of the gas sensitive film 92 substantially coincides with that of the resistive film 93.

The movable film structure 90 is fixed to the substrate 10 via the support portion (anchor) 45. The movable film structure 90 extends from a position, at which the movable film structure 90 is fixed to the substrate 10, in a predetermined direction parallel to the main surface of the substrate 10. In the embodiment, since the support portions 45 are respectively provided at both ends of the movable film structure 90, the movable film structure 90 extends in a predetermined direction parallel to a straight line on which the centers of both the support portions 45 are connected to each other.

The movable film structure 90 contains an area P1 located in a central portion, and areas P2 and P3 which are respectively positioned on both sides of the area P1. In the area P1, the resistive film 93 acts as a resistor for a heater, and as the upper electrode of the variable capacitor. In the areas P2 and P3, the resistive film 93 acts as a resistor for a heater.

In the areas P2 and P3, the resistive film 93 extends parallel to the aforementioned predetermined direction, and includes multiple wire-like wiring pattern portions which are disposed perpendicular to the aforementioned predetermined direction and are connected in series to each other. That is, in the areas P2 and P3, the pattern of the resistive film 93 includes mainly the pattern portions which extend parallel to the aforementioned predetermined direction.

As described above, the movable film structure 90 of the embodiment includes a stacked film configured with the insulating material film 91 acting as the base film, the gas sensitive film 92 that is deformed when absorbing or adsorbing the predetermined gas, and the resistive film 93 acting as a resistor for a heater. It is possible to obtain a gas detection device having good characteristics by adopting the movable film structure 90 having such a configuration. Hereinafter, additional description will be given.

If the gas sensitive film 92 absorbs or adsorbs the predetermined gas, the internal stress of the gas sensitive film 92 changes as it expands or shrinks as a result, and the gas sensitive film 92 is deformed. For this reason, if the gas sensitive film 92 absorbs or adsorbs the predetermined gas, the movable film structure 90 is deformed, and a distance between the first conductive portion 41 acting as the lower electrode of the variable capacitor and the resistive film 93 acting as the upper electrode of the variable capacitor changes. Since the amount of change of the gas sensitive film 92 changes according to the amount of absorption or adsorption of the predetermined gas, the distance between the first conductive portion (lower electrode) 41 and the resistive film (upper electrode) 93 also changes according to the amount of absorption or adsorption of the predetermined gas. Therefore, the capacitance of the variable capacitor formed by the first conductive portion (lower electrode) 41 and the resistive film (upper electrode) 93 changes according to the amount of absorption or adsorption of the predetermined gas. As a result, it is possible to calculate the amount of absorption or adsorption of the predetermined gas by obtaining the capacitance or change in capacitance of the variable capacitor. That is, it is possible to calculate the concentration of the predetermined gas in the vicinity of the gas sensitive film 92 by obtaining the capacitance or change in capacitance of the variable capacitor.

In the gas detection device based on the aforementioned principle, the heating of the gas sensitive film 92 may be required to satisfy a demand such as resetting the gas sensitive film 92 to an initial state by releasing residual gas from the gas sensitive film 92, or reducing humidity dependency of the gas detection device by releasing moisture from the gas sensitive film 92. In the embodiment, since the resistive film 93 provides a heater in the movable film structure 90, it is possible to heat the gas sensitive film 92 with the resistive film 93, and to satisfy the aforementioned requirement.

It may not be possible to sufficiently heat the gas sensitive film 92 using the resistive film 93 merely by providing the resistive film 93 for a heater in the movable film structure 90, which is a problem. In the embodiment, when viewed from the direction perpendicular to the main surface of the substrate 10, at least a portion of the pattern of the gas sensitive film 92 overlaps at least a portion of the pattern of the resistive film 93. For this reason, it is possible to efficiently transfer heat from the resistive film 93 to the gas sensitive film 92, and it is possible to sufficiently heat the gas sensitive film 92 via the resistive film 93. Particularly, when viewed from the direction perpendicular to the main surface of the substrate 10, the pattern of the gas sensitive film 92 coincides with that of the resistive film 93, and thus, it is possible to more efficiently heat the gas sensitive film 92. In addition, since the resistive film 93 is in contact with the gas sensitive film 92, it is possible to much more efficiently heat the gas sensitive film 92.

As such, in the gas detection device of the embodiment, it is possible to efficiently heat the gas sensitive film 92 using the resistive film 93, and thus, it is possible to accurately calculate the amount of absorption or adsorption of the predetermined gas. As a result, in the embodiment, it is possible to a high-performance gas detection device having good detection accuracy and good reliability.

In the embodiment, since the resistive film 93 acts as the second electrode (upper electrode or movable electrode) of the variable capacitor, it is not necessary to provide the second electrode of the variable capacitor in a special manner, and it is possible to simplify the configuration.

In the embodiment, in the areas P2 and P3 of the movable film structure 90, the pattern of the resistive film 93 includes mainly the multiple pattern portions which extend parallel to an extension direction (the predetermined direction) of the movable film structure 90. For this reason, when the gas sensitive film 92 absorbs or adsorbs the predetermined gas, the movable film structure 90 can be easily deformed perpendicular to the aforementioned predetermined direction. For this reason, it is possible to increase the amount of change of the distance between the first conductive portion (lower electrode) 41 and the resistive film (upper electrode) 93, and it is possible to increase the amount of change in the capacitance of the variable capacitor. As a result, it is possible to obtain a high-performance gas detection device having good detection accuracy (detection sensitivity).

Hereinafter, various modification examples of the gas detection device of the embodiment will be described. In each of the following modification examples, the basic configuration is the same as the configuration of the embodiment. Therefore, description of the items described in the embodiment will be omitted.

Figure 36:
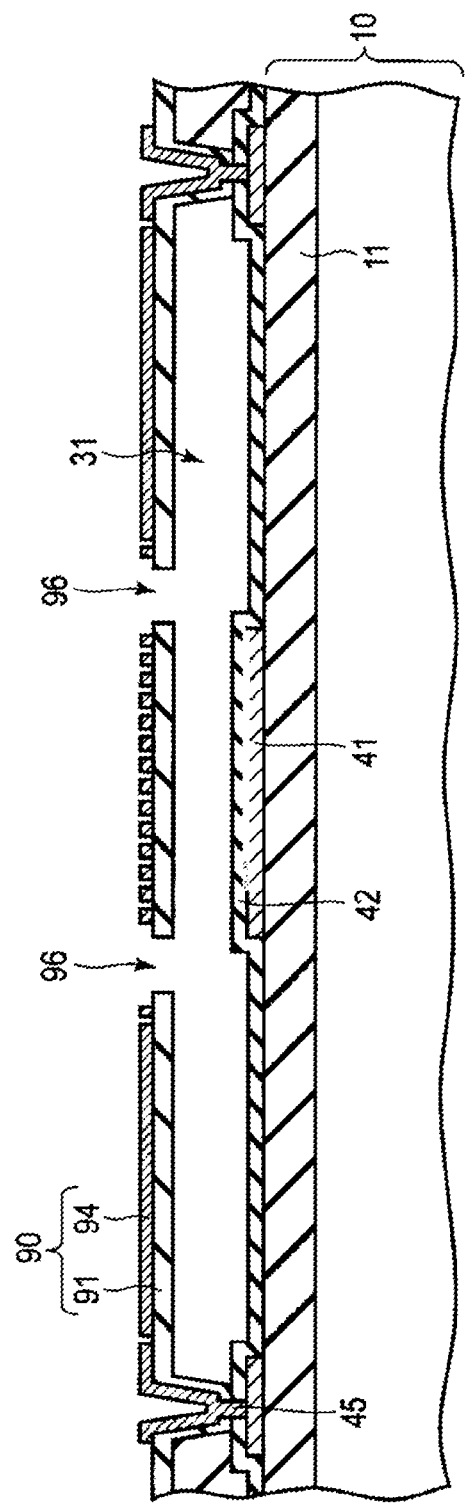
FIG. 36 is a schematic sectional view illustrating a configuration of a gas detection device in a first modification example of the fourth embodiment.
Figure 37:
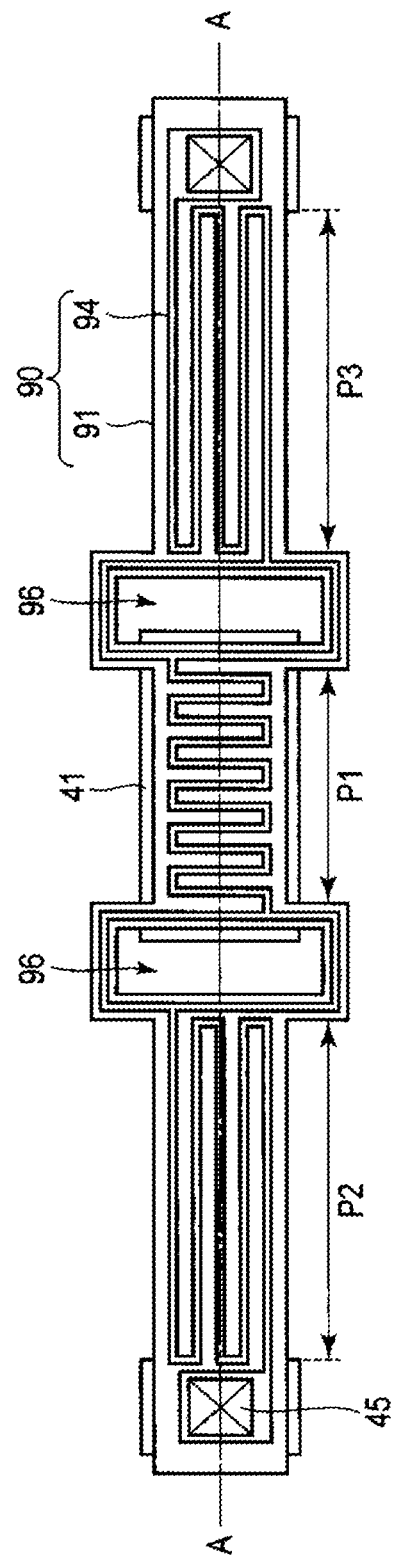
FIG. 37 is a schematic top view illustrating the configuration of the gas detection device in the first modification example of the fourth embodiment.

FIG. 36 is a schematic sectional view illustrating a configuration of a gas detection device in a first modification example of the third embodiment. FIG. 37 is a schematic top view illustrating the configuration of the gas detection device in the first modification example of the embodiment.

In the third embodiment, the gas sensitive film 92 is provided separately from the resistive film 93. In contrast, in this modification example, the gas sensitive film and the resistive film are configured as a single element. That is, in this modification example, the movable film structure 90 includes the insulating material film (first film) 91 formed of an insulating material, and a gas sensitive film (second film) 94 that is deformed when absorbing or adsorbing the predetermined gas, and which also acts as a resistor heating element. The insulating material film (first film) 91 is in contact with the gas sensitive film (second film) 94. The gas sensitive film 94 also acts as the second electrode (upper electrode or movable electrode) of the variable capacitor.

In the areas P2 and P3, the gas sensitive film 94 has the same pattern as those of the gas sensitive film 92 and the resistive film 93 of the third embodiment. That is, the gas sensitive film 94 includes multiple wire-like wiring pattern portions which extend parallel to a predetermined direction (the extension direction of the movable film structure 90), are disposed perpendicular to the predetermined direction (the extension direction of the movable film structure 90), and are connected in series to each other. That is, in the areas P2 and P3, the pattern of the gas sensitive film 94 includes mainly the pattern portions which extend parallel to the aforementioned predetermined direction.

In the modification example, the gas sensitive film 94 is also used as a resistive film for a heater. As a result, the gas sensitive film 94 can be efficiently heated by the gas sensitive film 94. Also, in the modification example, similar to the third embodiment, it is possible to obtain a high-performance gas detection device having good detection accuracy and good reliability.

In the modification example, since the gas sensitive film 94 acts as the second electrode (upper electrode or movable electrode) of the variable capacitor, it is not necessary to provide the second electrode of the variable capacitor in a special manner, and it is possible to simplify the configuration.

In this modification example, in the areas P2 and P3 of the movable film structure, the pattern of the gas sensitive film 94 includes mainly the multiple pattern portions which extend parallel to the extension direction (predetermined direction) of the movable film structure 90. As a result, also, in the modification example, similar to the embodiment, when the gas sensitive film 94 absorbs or adsorbs the predetermined gas, it is possible to increase the amount of change of the distance between the first conductive portion (lower electrode) 41 and the gas sensitive film (upper electrode) 94, and it is possible to obtain a high-performance gas detection device having good detection accuracy (detection sensitivity).

Figure 38:
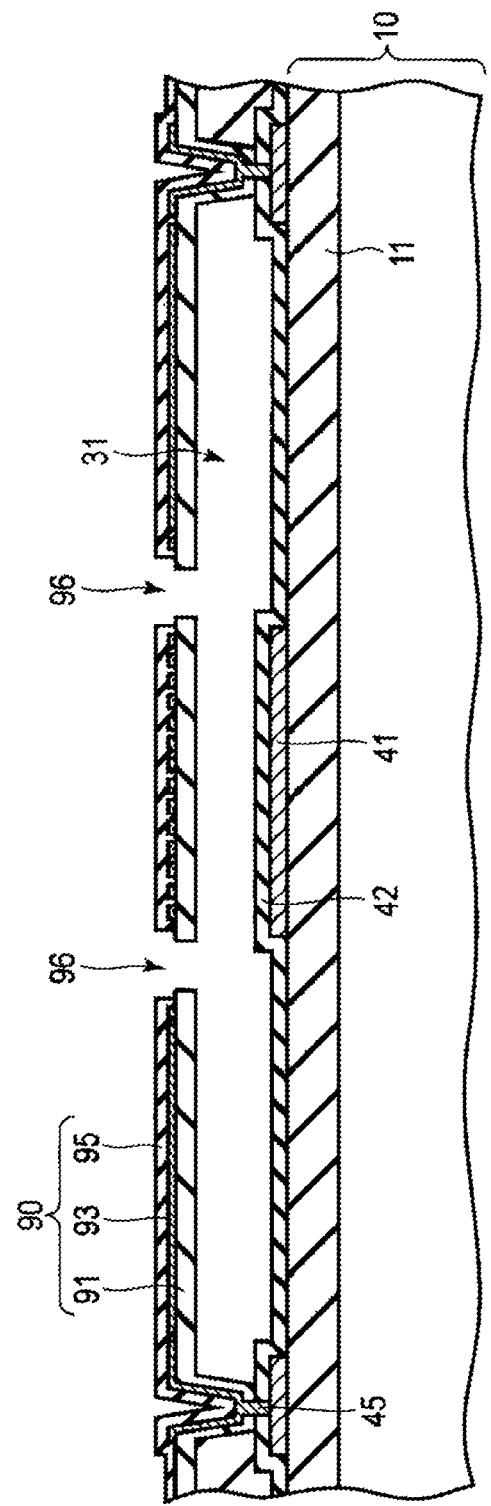
FIG. 38 is a schematic sectional view illustrating a configuration of a gas detection device in a second modification example of the fourth embodiment.
Figure 39:
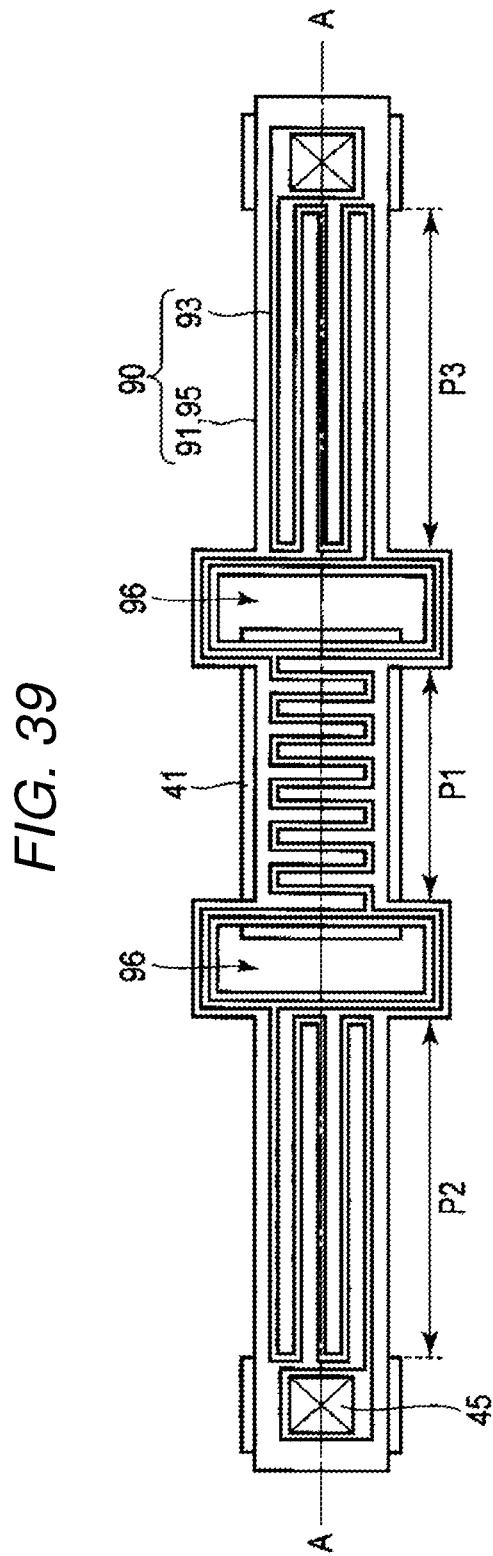
FIG. 39 is a schematic top view illustrating the configuration of the gas detection device in the second modification example of the fourth embodiment.

FIG. 38 is a schematic sectional view illustrating a configuration of a gas detection device in a second modification example of the embodiment. FIG. 39 is a schematic top view illustrating the configuration of the gas detection device in the second embodiment of the embodiment.

In the third embodiment, a conductive material is used as the material of the gas sensitive film 92. In contrast, in this modification example, an insulating material is used as the material of the gas sensitive film 92. That is, in this modification example, the movable film structure 90 includes the insulating material film (first film) 91 formed of an insulating material; a gas sensitive film (second film) 95 that is deformed when absorbing or adsorbing the predetermined gas, and is formed of an insulating material; and a resistive film (third film) 93 that acts as a resistor for a heater. The insulating material film 91 is in contact with the resistive film 93. The gas sensitive film 95 is in contact with the resistive film 93. The resistive film 93 also acts as the second electrode (upper electrode or movable electrode) of the variable capacitor.

If the gas sensitive film is formed of a conductive material as in the embodiment, it is necessary to prevent a short circuit of the resistive film 93 which is caused by the gas sensitive film. For this reason, there are limitations on the possible patterns of the gas sensitive film. In the modification example, since the gas sensitive film 95 is formed of an insulating material, there is no such limitation to the pattern of the gas sensitive film. In the modification example, the pattern of the gas sensitive film 95 is formed such that the pattern of the gas sensitive film 95 includes the pattern of the resistive film 93 when viewed from the direction perpendicular to the main surface of the substrate 10. Specifically, when viewed from the direction perpendicular to the main surface of the substrate 10, the pattern of the gas sensitive film 95 substantially coincides with that of the resistive film 91.

The gas detection device of the modification example also has the same basic configuration as that of the third embodiment, and it is possible to obtain the same effects as those of the embodiment.

In this modification example, since the gas sensitive film 95 is formed of an insulating material, it is possible to form the pattern of the gas sensitive film 95 without significant limitation on the pattern geometry.

Figure 40:
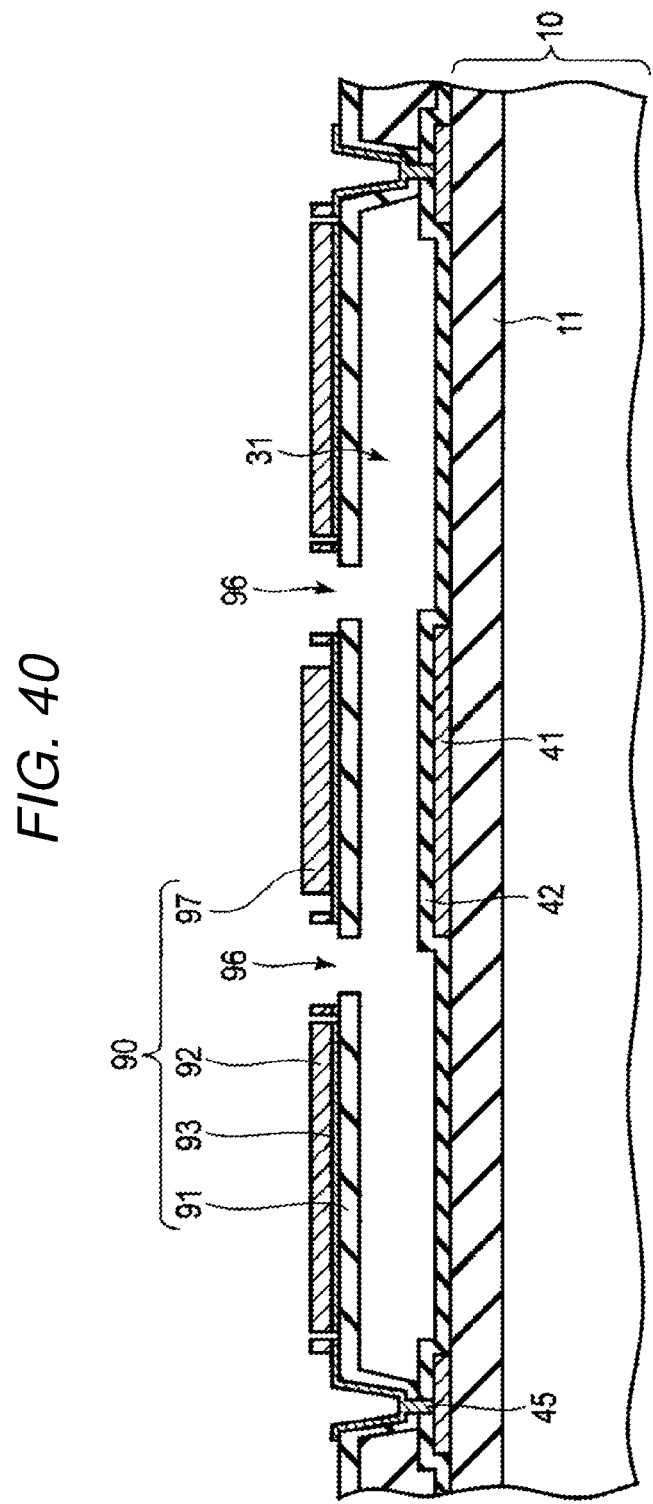
FIG. 40 is a schematic sectional view illustrating a configuration of a gas detection device in a third modification example of the fourth embodiment.
Figure 41:
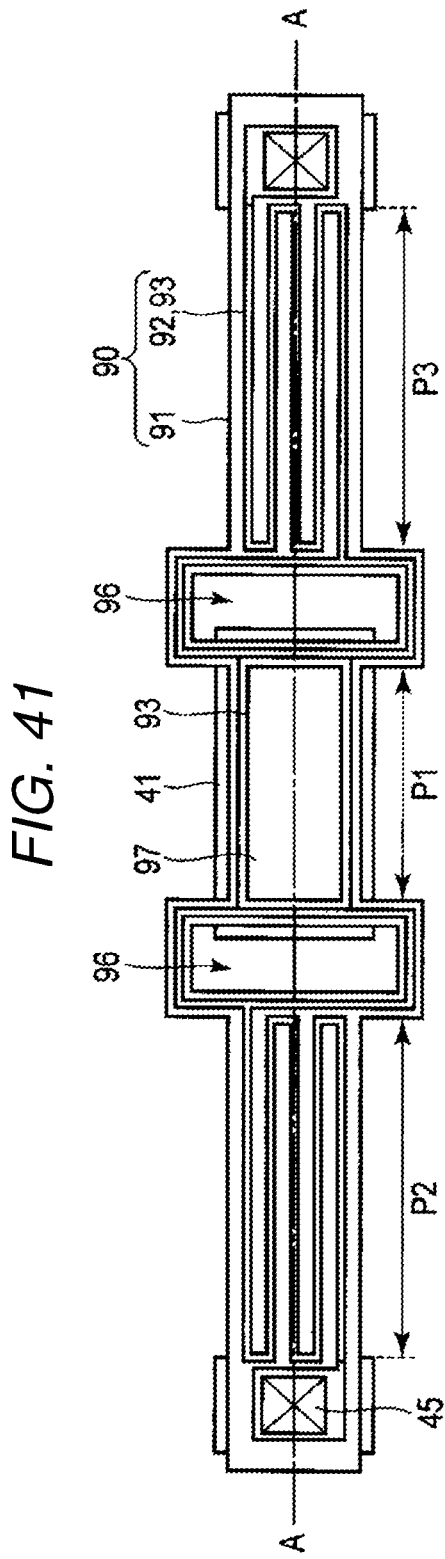
FIG. 41 is a schematic top view illustrating the configuration of the gas detection device in the third modification example of the fourth embodiment.

FIG. 40 is a schematic sectional view illustrating a configuration of a gas detection device in a third modification example of the embodiment. FIG. 41 is a schematic top view illustrating the configuration of the gas detection device in the third modification example of the third embodiment.

In the third embodiment, the resistive film 93 is also used as the second electrode (upper electrode or movable electrode) of the variable capacitor. In contrast, in the modification example, the second electrode of the variable capacitor is provided separately from the resistive film 93. Specifically, in the modification example, a movable electrode film 97 is provided in the area P1. That is, in the modification example, the movable film structure 90 includes the insulating material film (first film) 91 formed of an insulating material; the gas sensitive film (second film) 92 that is deformed when absorbing or adsorbing the predetermined gas; the resistive film (third film) 93 that acts as a resistor for a heater; and the movable electrode film 97 that acts as the second electrode of the variable capacitor. In the area P1, the movable electrode film 97 is in contact with the resistive film 93. Ti, Ni, Cu, Al, or the like may be used as the material of the movable electrode film 97.

The gas detection device of this modification example also has the same basic configuration as that of the third embodiment, and it is possible to obtain the same effects as those of the embodiment.

In this modification example, since the movable electrode film 97 acting as the second electrode of the variable capacitor is provided separately from the resistive film 93, it is possible to increase the size of the pattern of the movable electrode film 97. That is, in the third embodiment, since the resistive film 93 is used as the second electrode of the variable capacitor, the second electrode of the variable capacitor has a wire-like wiring pattern including bent portions. In contrast, in this modification example, since the second electrode of the variable capacitor has a rectangular pattern, it is possible to increase the size of the pattern. As a result, it is possible to increase the capacitance of the variable capacitor, and to improve gas detection sensitivity.

Figure 42:
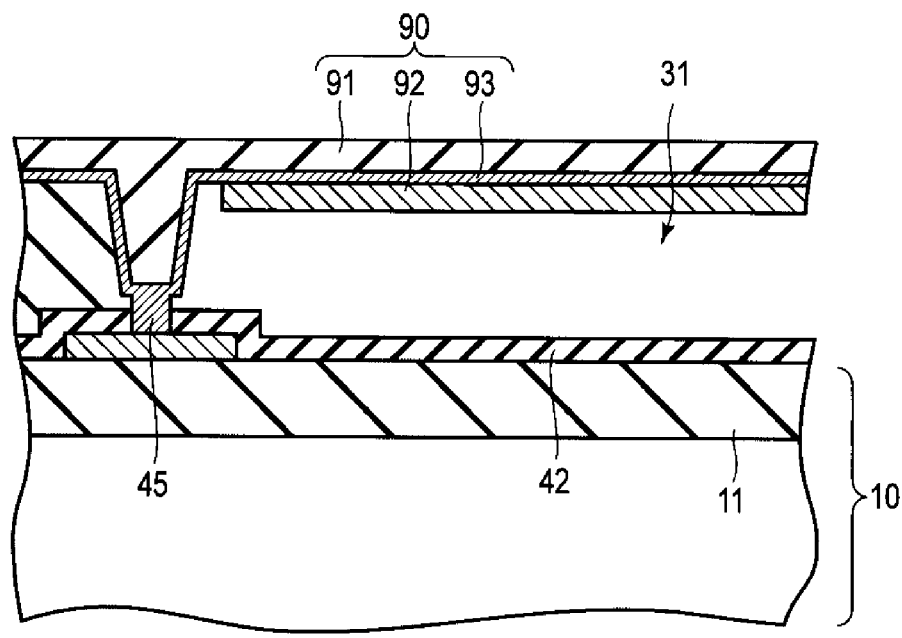
FIG. 42 is a schematic sectional view illustrating a configuration of a gas detection device in a fourth modification example of the fourth embodiment.

FIG. 42 is a schematic sectional view illustrating a configuration of a gas detection device in a fourth modification example of the third embodiment.

In the third embodiment, the gas sensitive film (second film) 92 and the resistive film (third film) 93 are provided on the upper surface side (outer surface side) of the insulating material film (first film) 91. In contrast, in this modification example, the gas sensitive film (second film) 92 and the resistive film (third film) 93 are provided on the lower surface side (inner surface side) of the insulating material film (first film) 91. The rest of the basic configuration is the same as the configuration of the third embodiment. A conductive material or an insulating material may be used as the material of the gas sensitive film 92.

The gas detection device of this modification example also has the same basic configuration as that of the embodiment, and it is possible to obtain the same effects as those of the third embodiment.

Figure 43:
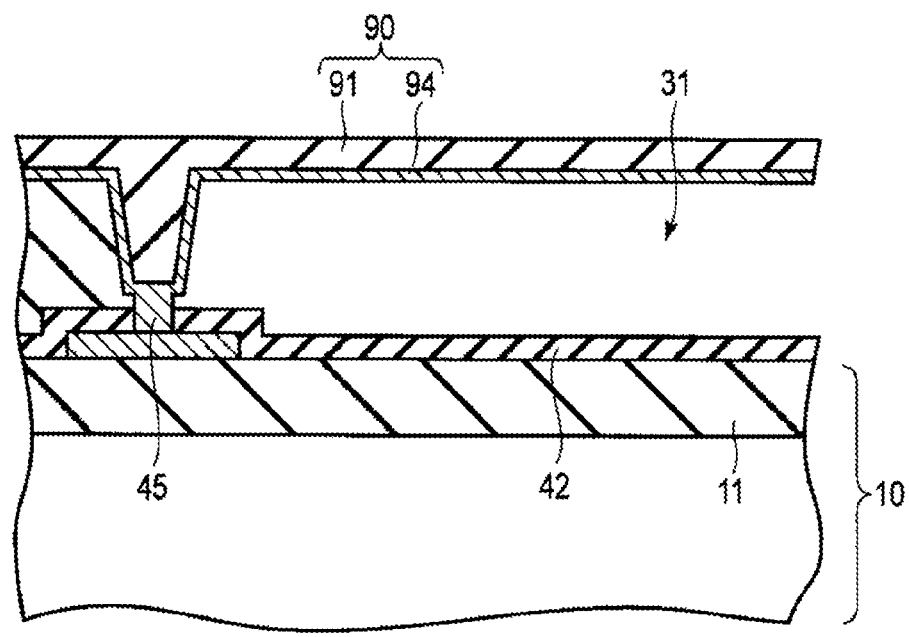
FIG. 43 is a schematic sectional view illustrating a configuration of a gas detection device in a fifth modification example of the fourth embodiment.

FIG. 43 is a schematic sectional view illustrating a configuration of a gas detection device in a fifth modification example of the third embodiment.

In the first modification example (refer to FIGS. 36 and 37) of the third embodiment, the gas sensitive film (second film) 94 is provided on the upper surface side (outer surface side) of the insulating material film (first film) 91. In this modification example, the gas sensitive film (second film) 94 is provided on the lower surface side (inner surface side) of the insulating material film (first film) 91.

The gas detection device of this modification example also has the same basic configuration as those of the third embodiment and the first modification example of the embodiment, and it is possible to obtain the same effects as those of the third embodiment and the first modification example of the third embodiment.

Figure 44:
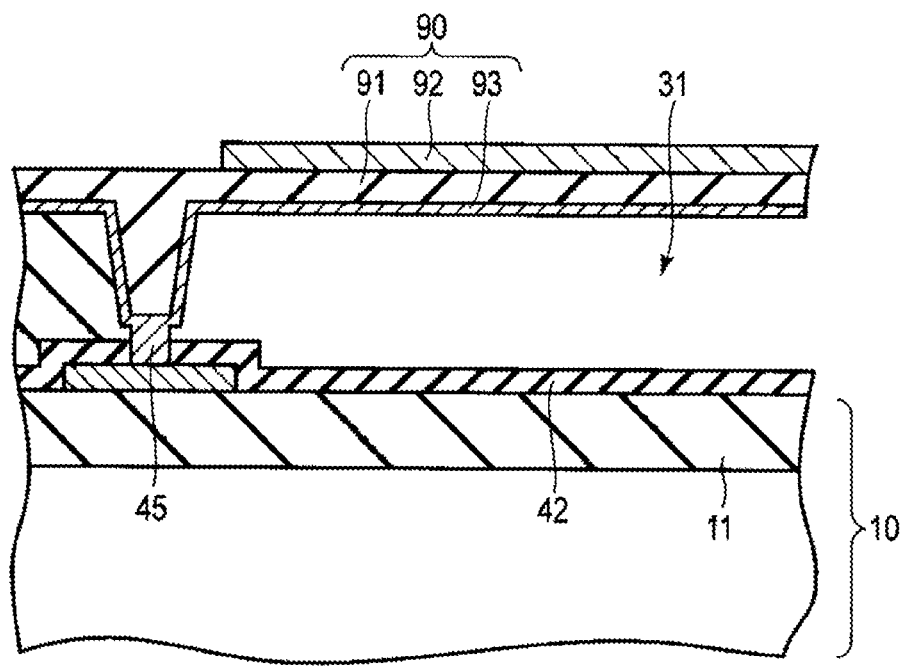
FIG. 44 is a schematic sectional view illustrating a configuration of a gas detection device in a sixth modification example of the fourth embodiment.

FIG. 44 is a schematic sectional view illustrating a configuration of a gas detection device in a sixth modification example of the third embodiment.

In the third embodiment, the gas sensitive film (second film) 92 is in contact with the resistive film (third film) 93. In contrast, in this modification example, the gas sensitive film (second film) 92 is not in contact with the resistive film (third film) 93. In the example illustrated in FIG. 44, the gas sensitive film (second film) 92 is formed on the upper surface side of the insulating material film (first film) 91, and the resistive film (third film) 93 is formed on the lower surface side of the insulating material film (first film) 91. Alternatively, the gas sensitive film (second film) 92 may be formed on the lower surface side of the insulating material film (first film) 91, and the resistive film (third film) 93 may be formed on the upper surface side of the insulating material film (first film) 91.

The gas detection device of this modification example also has the same basic configuration as that of the third embodiment, and it is possible to obtain the same effects as those of the embodiment.

In this modification example, the gas sensitive film 92 is electrically insulated from the resistive film 93 by the insulating material film 91. As a result, even if a conductive material is used as the material of the gas sensitive film 92, it is possible to prevent a short circuit of the resistive film 93 which is caused by contact with the gas sensitive film 92, and it is possible to form the pattern of the gas sensitive film 92 without significant limitation on the geometry thereof.

If the gas sensitive film 92 formed of a conductive material is in contact with the resistive film 93 formed of a conductive material as in the embodiment (refer to FIGS. 34 and 35), and the resistance value of the gas sensitive film 92 is less than that of the resistive film 93, the resistance value of a stacked film configured with the gas sensitive film 92 and the resistive film 93 is much less than that of only the resistive film 93. For this reason, the resistive film 93 does not satisfactorily act as a heater, which is a problem. In this modification example, since the gas sensitive film 92 is not electrically connected to the resistive film 93, it is possible to prevent the occurrence of such a problem.

A film having a relatively high thermal conductivity and/or having a thin thickness is preferably used as the insulating material film 91. It is possible to efficiently heat the gas sensitive film 92 by using such a film as the insulating material film 91.

Figure 45:
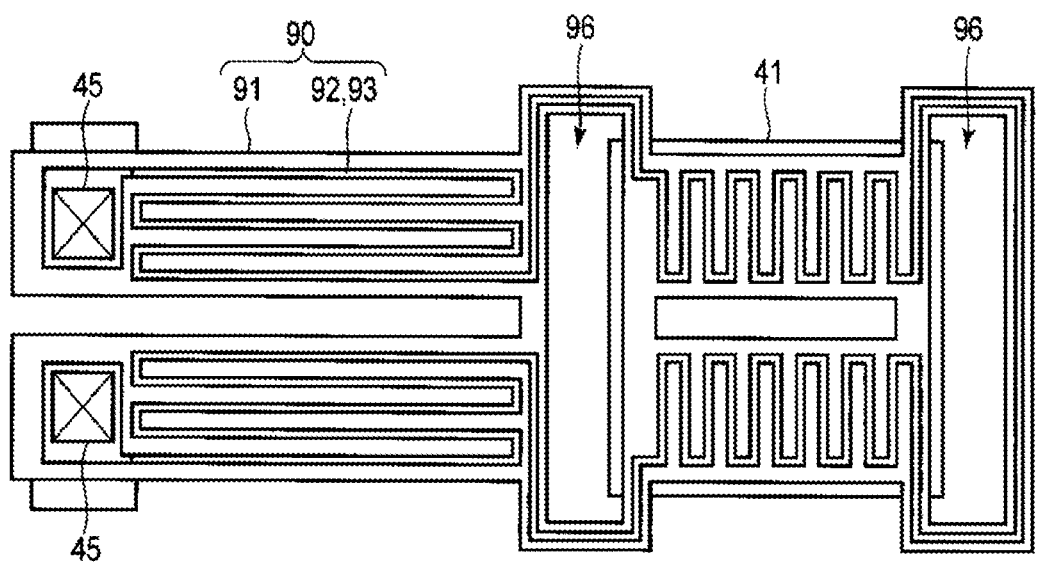
FIG. 45 is a schematic top view illustrating a configuration of a gas detection device in a seventh modification example of the fourth embodiment.

FIG. 45 is a schematic top view illustrating a configuration of a gas detection device in a seventh modification example of the third embodiment.

In the third embodiment, the movable film structure 90 is fixed to the substrate 10 via the support portions (anchors) 45 which are respectively on both sides of the movable film structure 90. In contrast, in this modification example, the movable film structure 90 is fixed to the substrate 10 via the support portion (anchor) 45 that is provided on one side of the movable film structure 90. The rest of the basic configuration is the same as the configuration of the third embodiment.

The gas detection device of this modification example has the same basic configuration as that of the embodiment, and it is possible to obtain the same effects as those of the third embodiment.

Figure 46:
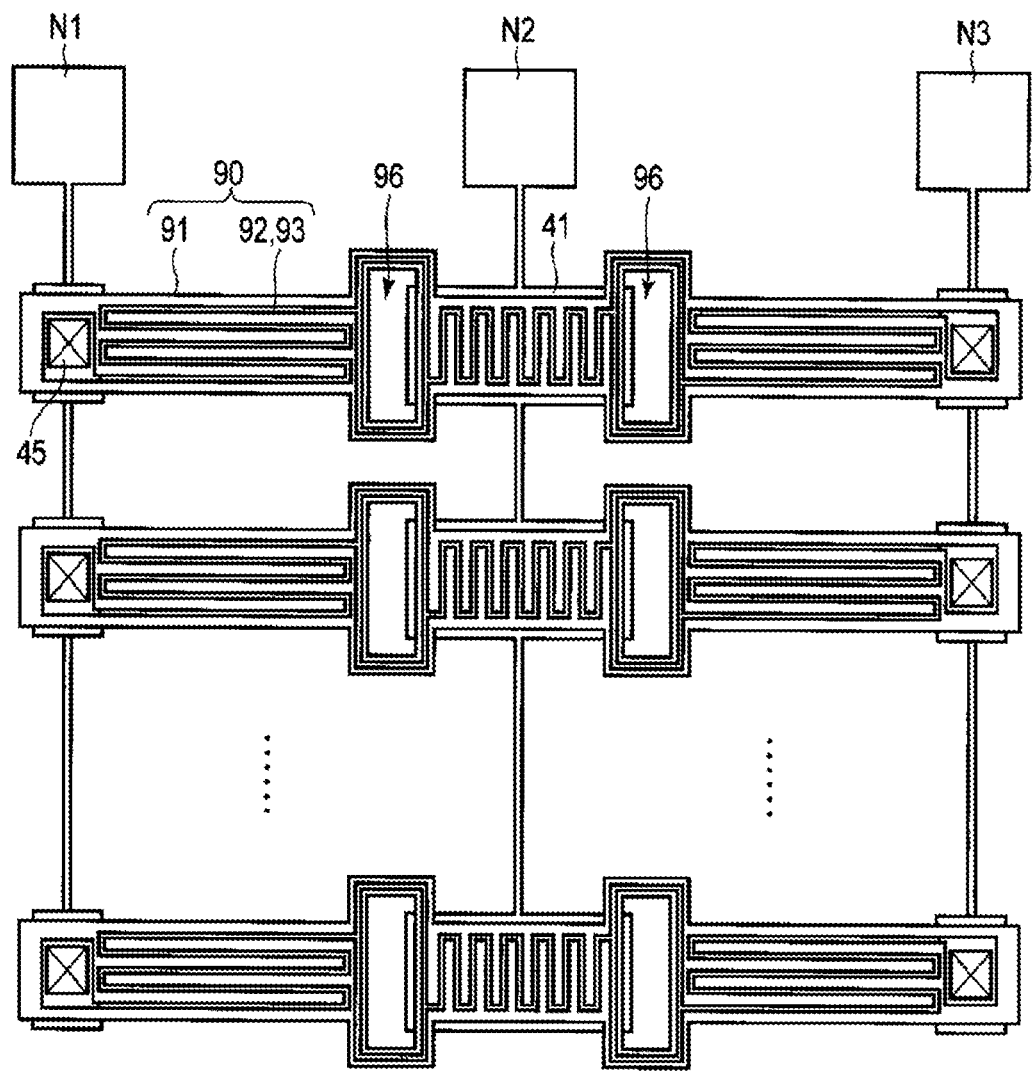
FIG. 46 is a schematic top view illustrating a configuration of a gas detection device in an eighth modification example of the fourth embodiment.

FIG. 46 is a schematic top view illustrating a configuration of a gas detection device in an eighth modification example of the third embodiment.

The gas detection device of this modification example is provided with multiple MEMS element units illustrated in the third embodiment and the aforementioned various modification examples.

A first end of each of the multiple movable film structures 90 is electrically connected to a node (terminal) N1, and a second end of each of the multiple movable film structures 90 is electrically connected to a node (terminal) N3. The lower electrode (fixed electrode or first conductive portion) 41 of each of multiple variable capacitors is electrically connected to a node (terminal) N2. When current flows through the resistive film 93 forming a heater, a voltage is applied between the node N1 and the node N3. A capacitance between the node N1 (or the node N3) and the node N2 is measured to monitor the capacitance of each of the variable capacitors.

In the gas detection device of this modification example, each of the MEMS element units has the same basic configuration as that of the embodiment, and it is possible to obtain the same effects as those of the third embodiment.

In this modification example, since the multiple MEMS element units are provided, it is possible to improve gas detection accuracy.

The configurations of the third embodiment and the first to eighth modification examples thereof may be suitably combined together.

In the third embodiment and the first to eighth modification examples thereof, if a conductive material is used as the material of the gas sensitive film, the pattern of the gas sensitive film substantially coincides with that of the resistive film when viewed from the direction perpendicular to the main surface of the substrate. If an insulating material is used as the material of the gas sensitive film, or the gas sensitive film is electrically insulated from the resistive film, there is no significant limitation to the pattern of the gas sensitive film, and the pattern of the gas sensitive film may include the pattern of the resistive film when viewed from the direction perpendicular to the main surface of the substrate.

Hereinafter, the system configuration and the operation of the gas detection device of the embodiment will be described.

Figure 47:
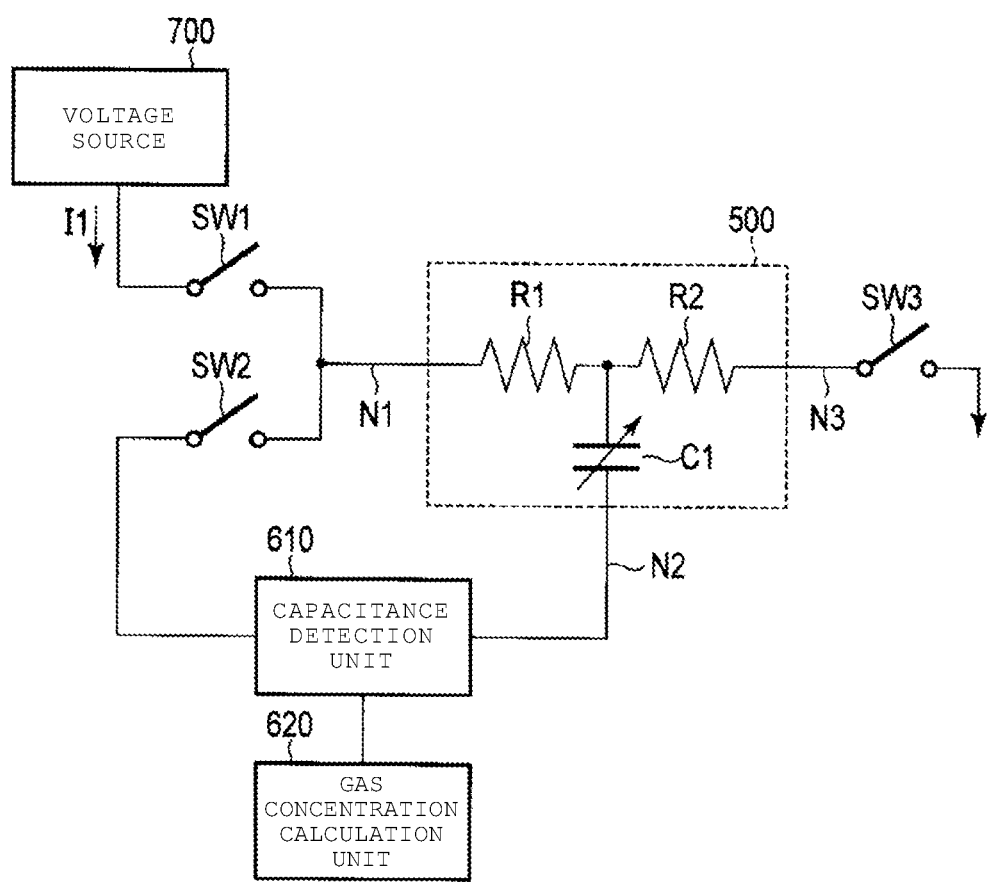
FIG. 47 is a diagram illustrating an example of the entire system configuration of the gas detection device in the fourth embodiment.

FIG. 47 is a diagram illustrating an example of a system configuration of the gas detection device in the embodiment.

As illustrated in FIG. 47, an equivalent circuit of a MEMS element unit 500 is represented by a resistor R1, a resistor R2, and a variable capacitor C1. The node N2 is connected to a capacitance detection unit 610 that detects the capacitance of the variable capacitor C1. The capacitance detection unit 610 is connected to a gas concentration calculation unit 620 that calculates the concentration of gas based on the capacitance detected by the capacitance detection unit 610. It is possible to calculate the concentration of gas with high accuracy via the gas concentration calculation unit 620 by obtaining a relationship between the capacitance of the variable capacitor C1 and the concentration of gas in advance. Switches SW1 and SW2 are connected to the node N1, and a switch SW3 is connected to the node N3. A voltage source 700 is connected to the switch SW1, and the capacitance detection unit 610 is connected to the switch SW2.

Figure 48A:
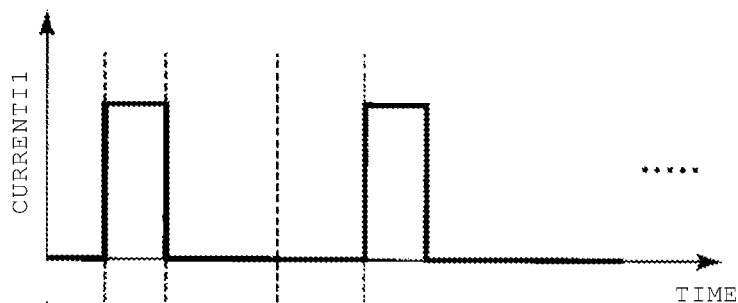
FIGS. 48A and 48B show a timing chart illustrating examples of the operation of the gas detection device in the fourth embodiment.
Figure 48B:
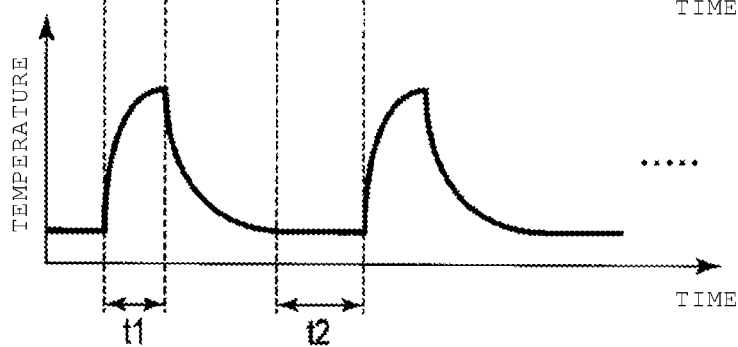

FIGS. 48A and 48B show a timing chart illustrating an example of the operation of the gas detection device of the embodiment. FIG. 48A illustrates a change over time in current that is supplied from the voltage source 700 to the resistors R1 and R2. FIG. 48B illustrates a change over time in the temperature of the gas sensitive film.

At time t1, the switches SW1 and SW3 in FIG. 47 are turned on, and current is supplied from the voltage source 700 to the resistors R1 and R2 for time period t1. As a result, the resistors R1 and R2 generate heat, and the temperature of the gas sensitive film increases. After the switches SW1 and SW3 are turned off, at time t2, the switch SW2 is turned on, and the capacitance detection unit 610 detects the capacitance of the variable capacitor C1. In the example illustrated in FIGS. 48A and 48B, the capacitance of the variable capacitor C1 is detected during time period t2 after the temperature of the gas sensitive film decreases to a normal temperature.

Figure 49A:
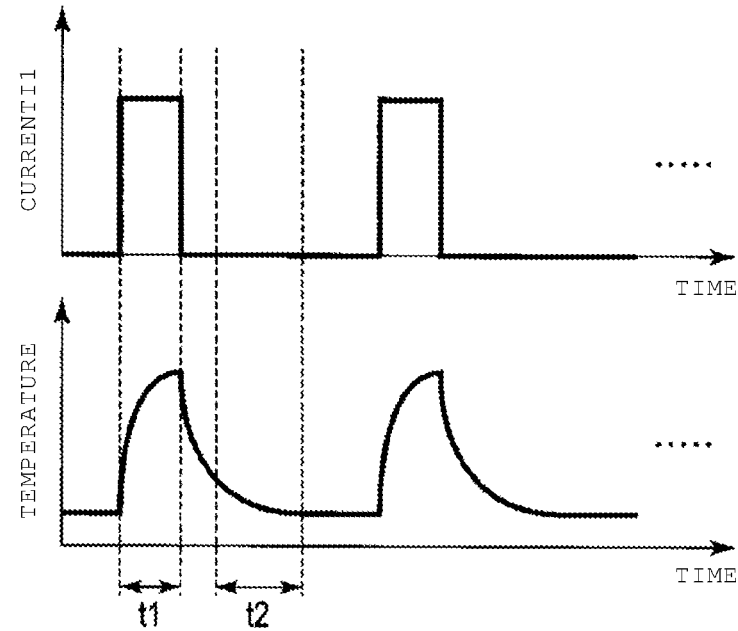
FIGS. 49A and 49B show timing charts illustrating another example of the operation of the gas detection device in the fourth embodiment.
Figure 49B:
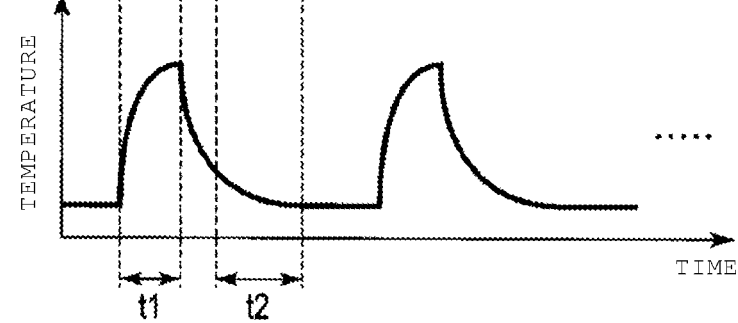

FIGS. 49A and 49B show a timing chart illustrating another example of the operation of the gas detection device in the embodiment. The basic operation is the same as the operation illustrated in FIGS. 48A and 48B. In this example, the capacitance of the variable capacitor C1 is detected during time period t2 before the temperature of the gas sensitive film decreases to a normal temperature.

Figure 50:
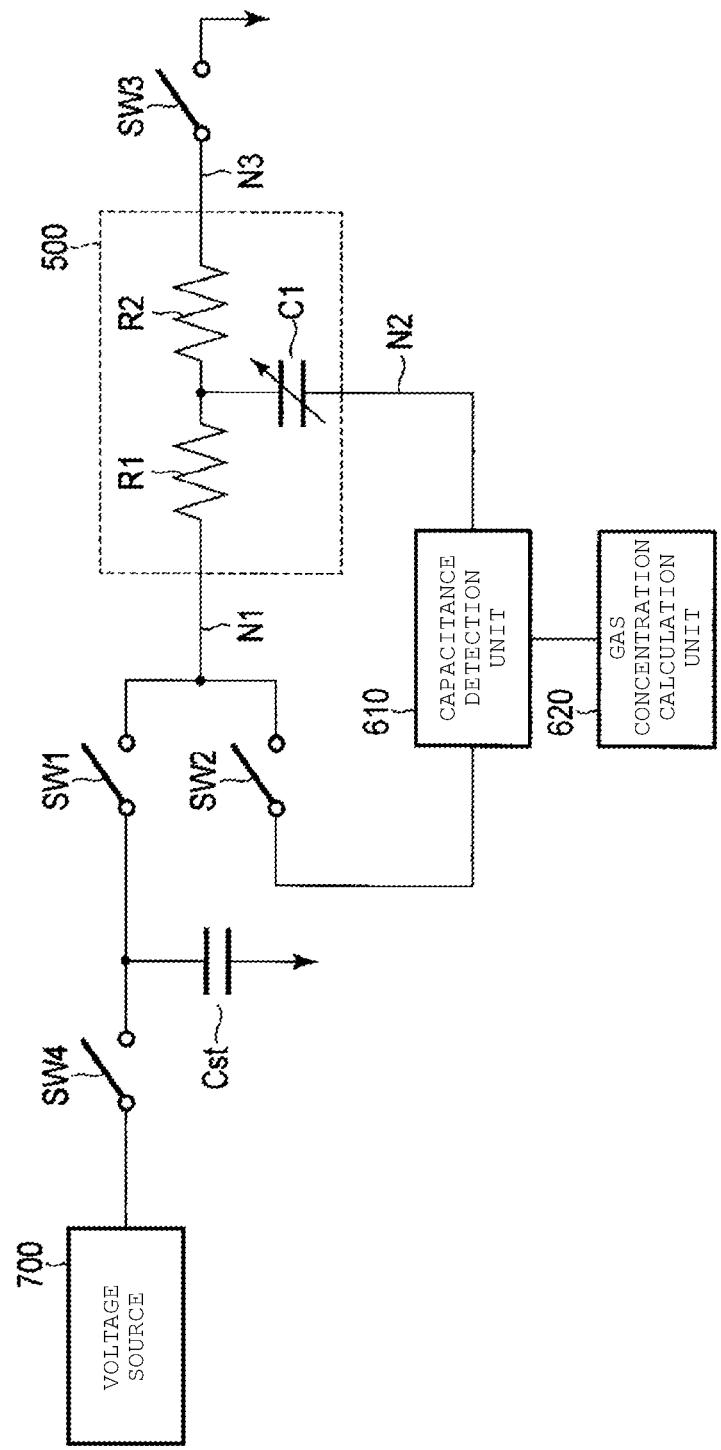
FIG. 50 is a diagram illustrating another example of the entire system configuration of the gas detection device in the fourth embodiment.

FIG. 50 is a diagram illustrating another example of a system configuration of the gas detection device in the embodiment. The basic configuration illustrated in FIG. 50 is the same as that illustrated in FIG. 47. In this configuration example, a capacitor Cst having a large capacitance is connected to the voltage source 700 via a switch SW4. It is possible to allow current to quickly flow through the resistors R1 and R2 by charging the capacitor Cst with voltage from the voltage source 700. As a result, it is possible to cause the gas sensitive film to rapidly generate heat, and to thus rapidly heat the gas sensitive film.

Hereinafter, contents of the embodiment are appended. brittle[0170]While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A gas detection device, comprising:
   a substrate; and
   a movable film structure, a portion of which extends over and is spaced from the substrate so that a cavity is provided between the portion of the movable film structure and the substrate, the movable film structure having a plurality of through holes leading to the cavity, the movable film structure including a first film of an insulating material and a second film which deforms as a result of absorbing or adsorbing a predetermined gas.

2. The gas detection device according to claim 1, wherein the movable film structure further includes a moisture preventive film that covers the second film.

3. The gas detection device according to claim 1, further comprising:
   a heating unit that heats the second film.

4. The gas detection device according to claim 1, wherein the insulating material comprises a brittle material.

5. The gas detection device according to claim 1, wherein the first film comprises silicon (Si).

6. The gas detection device according to claim 1, wherein the first film comprises at least one of silicon nitride, silicon oxide, and silicon carbide.

7. The gas detection device according to claim 1, wherein the predetermined gas is hydrogen, a hydrogen-containing gas, water vapor, or a volatile organic compound gas.

8. The gas detection device according to claim 1, wherein the movable film structure further comprises a resistive film.

9. The gas detection device according to claim 1, wherein
   a portion of the movable film structure extends from a position at which the movable film structure is fixed to the substrate, and
   the portion of the movable film structure is spaced from the substrate and movable with respect to the substrate in parallel to the main surface of the substrate.

10. The gas detection device according to claim 9, wherein a portion of the second film extends from the position at which the movable film structure is fixed to the substrate.

11. The gas detection device according to claim 1, wherein the predetermined gas is hydrogen or a hydrogen-containing gas.

12. The gas detection device according to claim 11, wherein the second film comprises one of palladium (Pd), an alloy containing palladium (Pd), an alloy containing titanium (Ti), or an alloy containing lanthanum (La).

13. The gas detection device according to claim 1, further comprising:
   a first conductive portion located on the substrate, the first conductive portion forming a first electrode of a variable capacitor, wherein
   the movable film structure includes a portion thereof forming a second electrode of the variable capacitor.

14. The gas detection device according to claim 13, wherein
   a portion of the movable film structure extends from a position at which the movable film structure is fixed to the substrate, and the portion of the movable film structure located over and spaced from the substrate extends in a predetermined direction parallel to the main surface of the substrate, and
   the second electrode comprises multiple wiring pattern portions connected in series to one another, some of the multiple wiring pattern portions being in parallel to the predetermined direction, some of the multiple wiring pattern portions being perpendicular to the predetermined direction.

15. The gas detection device according to claim 1, wherein the movable film structure is fixed to the substrate via an anchor support portion.

16. The gas detection device according to claim 15, wherein the second film extends from the anchor support portion.

17. The gas detection device according to claim 1, further comprising:
   a first conductive portion on the substrate, the first conductive portion forming a first electrode of a variable capacitor; and
   a second conductive portion forming a second electrode of the variable capacitor, the second electrode being connected to the movable film structure.

18. The gas detection device according to claim 17, wherein the second electrode is connected to the first film of the movable film structure via an anchor connection portion.

19. The gas detection device according to claim 18, wherein the first film has a cap structure.

20. The gas detection device according to claim 18, further comprising:
   a heating unit that heats the second film.

* * * * *